United States Patent
Ta et al.

(10) Patent No.: US 11,517,457 B2
(45) Date of Patent: Dec. 6, 2022

(54) INTRAVASCULAR STENT

(71) Applicant: ABBOTT CARDIOVASCULAR SYSTEMS INC., Santa Clara, CA (US)

(72) Inventors: Diem Ta, San Jose, CA (US); Erik Eli, Redwood City, CA (US); Senthil Eswaran, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 16/503,093

(22) Filed: Jul. 3, 2019

(65) Prior Publication Data

US 2021/0000625 A1    Jan. 7, 2021

(51) Int. Cl.
*A61F 2/915* (2013.01)
*A61L 31/02* (2006.01)

(52) U.S. Cl.
CPC ............ *A61F 2/915* (2013.01); *A61L 31/022* (2013.01); *A61F 2002/91533* (2013.01); *A61F 2002/91566* (2013.01)

(58) Field of Classification Search
None
See application file for complete search history.

(56) References Cited

U.S. PATENT DOCUMENTS

| | | |
|---|---|---|
| 5,807,404 A | 9/1998 | Richter |
| 5,810,842 A | 9/1998 | Di Fiore et al. |
| 5,827,321 A | 10/1998 | Roubin et al. |
| 5,913,895 A | 6/1999 | Burpee et al. |
| 6,022,371 A | 2/2000 | Killion |
| 6,022,374 A | 2/2000 | Imran |
| 6,039,756 A | 3/2000 | Jang |
| 6,042,505 A | 3/2000 | Bellinger et al. |
| 6,107,395 A | 8/2000 | Rosthauser et al. |
| 6,179,867 B1 | 1/2001 | Cox |
| 6,179,868 B1 | 1/2001 | Burpee et al. |
| 6,183,506 B1 | 2/2001 | Penn et al. |
| 6,325,821 B1 | 12/2001 | Gaschino et al. |
| 6,348,065 B1 | 2/2002 | Brown et al. |
| 6,416,539 B1 | 7/2002 | Hassdenteufel |
| 6,786,922 B2 | 9/2004 | Schaeffer |
| 6,790,227 B2 | 9/2004 | Burgermeister |
| 6,796,999 B2 | 9/2004 | Pinchasik |
| 6,805,707 B1 | 10/2004 | Hong et al. |
| 6,896,696 B2 | 5/2005 | Doran et al. |
| 6,918,928 B2 | 7/2005 | Wolinsky et al. |
| 7,316,710 B1 | 1/2008 | Cheng et al. |

(Continued)

FOREIGN PATENT DOCUMENTS

WO    9822159 A2    5/1998

OTHER PUBLICATIONS

International Search Report for PCT/US20/32912 dated Aug. 19, 2020.

*Primary Examiner* — Leslie Lopez
(74) *Attorney, Agent, or Firm* — Fulwider Patton LLP

(57) ABSTRACT

An expandable stent for implantation in a body lumen, such as an artery, is disclosed. The stent consists of a plurality of radially expandable cylindrical rings generally aligned on a common longitudinal stent axis and interconnected by one or more interconnecting links placed so that the stent is flexible in the longitudinal direction. The link pattern is optimized to enhance longitudinal flexibility and high longitudinal strength compression of the stent.

5 Claims, 23 Drawing Sheets

(56) References Cited

U.S. PATENT DOCUMENTS

| | | |
|---|---|---|
| 7,465,315 B2 | 12/2008 | Morris et al. |
| 7,491,228 B2 | 2/2009 | Doran et al. |
| 8,029,558 B2 | 10/2011 | Ta et al. |
| 8,142,489 B2 | 3/2012 | Doran et al. |
| 8,372,137 B2 | 2/2013 | Pienknagura |
| 8,801,773 B2 | 8/2014 | Doran et al. |
| 9,603,727 B2 | 3/2017 | Ta et al. |
| 9,675,480 B2 | 6/2017 | Gomez et al. |
| 2002/0198593 A1* | 12/2002 | Gomez ................ A61F 2/91 623/1.16 |
| 2004/0143318 A1 | 6/2004 | Tseng et al. |
| 2005/0101624 A1* | 5/2005 | Betts ................ A61P 37/06 514/291 |
| 2008/0086194 A1* | 4/2008 | Kreidler ............ A61F 2/915 623/1.15 |
| 2011/0208286 A1* | 8/2011 | Ta .................... A61F 2/958 623/1.11 |
| 2013/0123905 A1 | 5/2013 | Abunassar et al. |
| 2013/0226283 A1 | 8/2013 | Abunassar et al. |
| 2016/0081827 A1* | 3/2016 | Lumauig ............ A61F 2/915 264/28 |
| 2019/0021889 A1 | 1/2019 | Ta et al. |

* cited by examiner

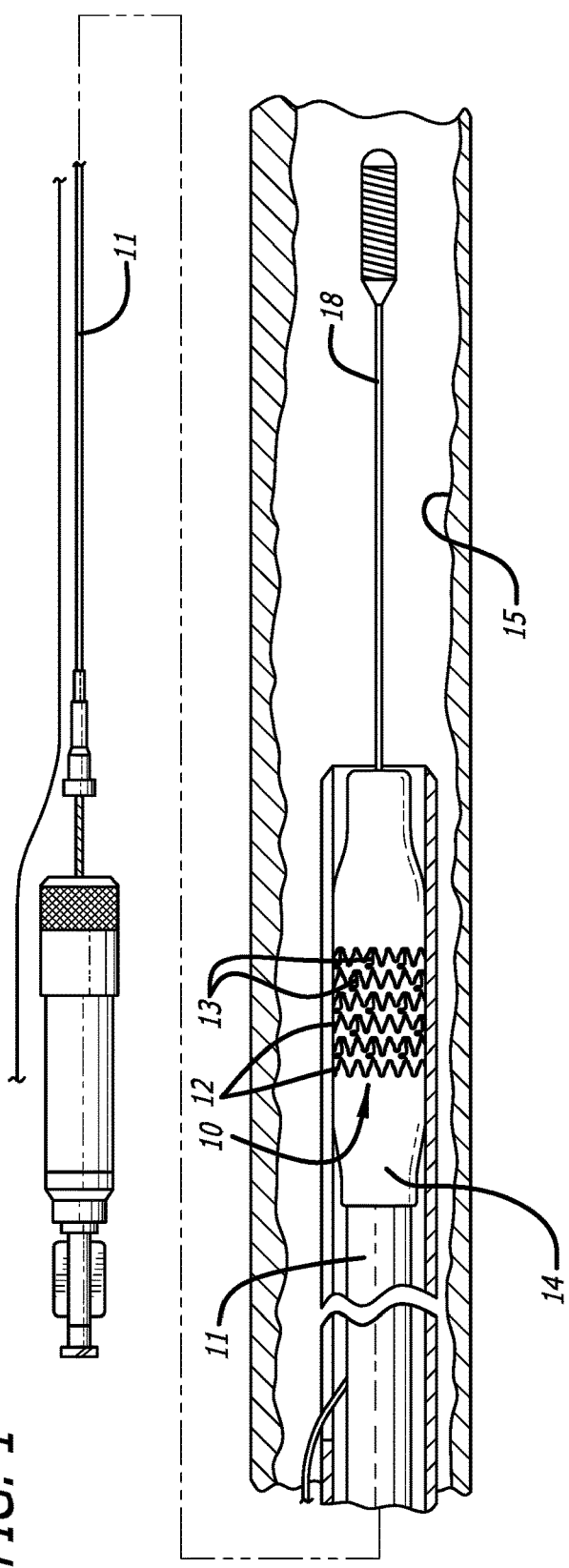
FIG. 1
FIG. 2
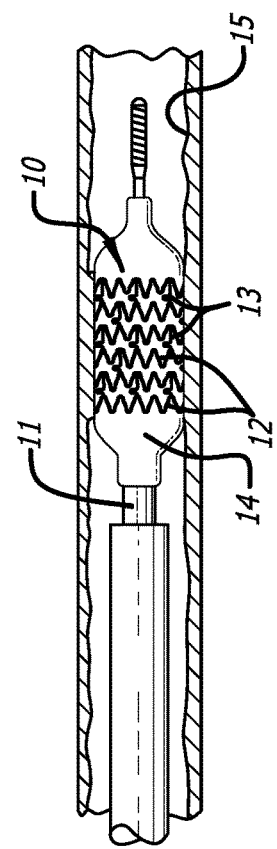
FIG. 3
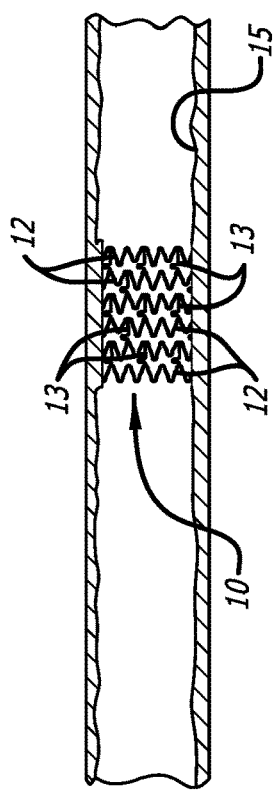

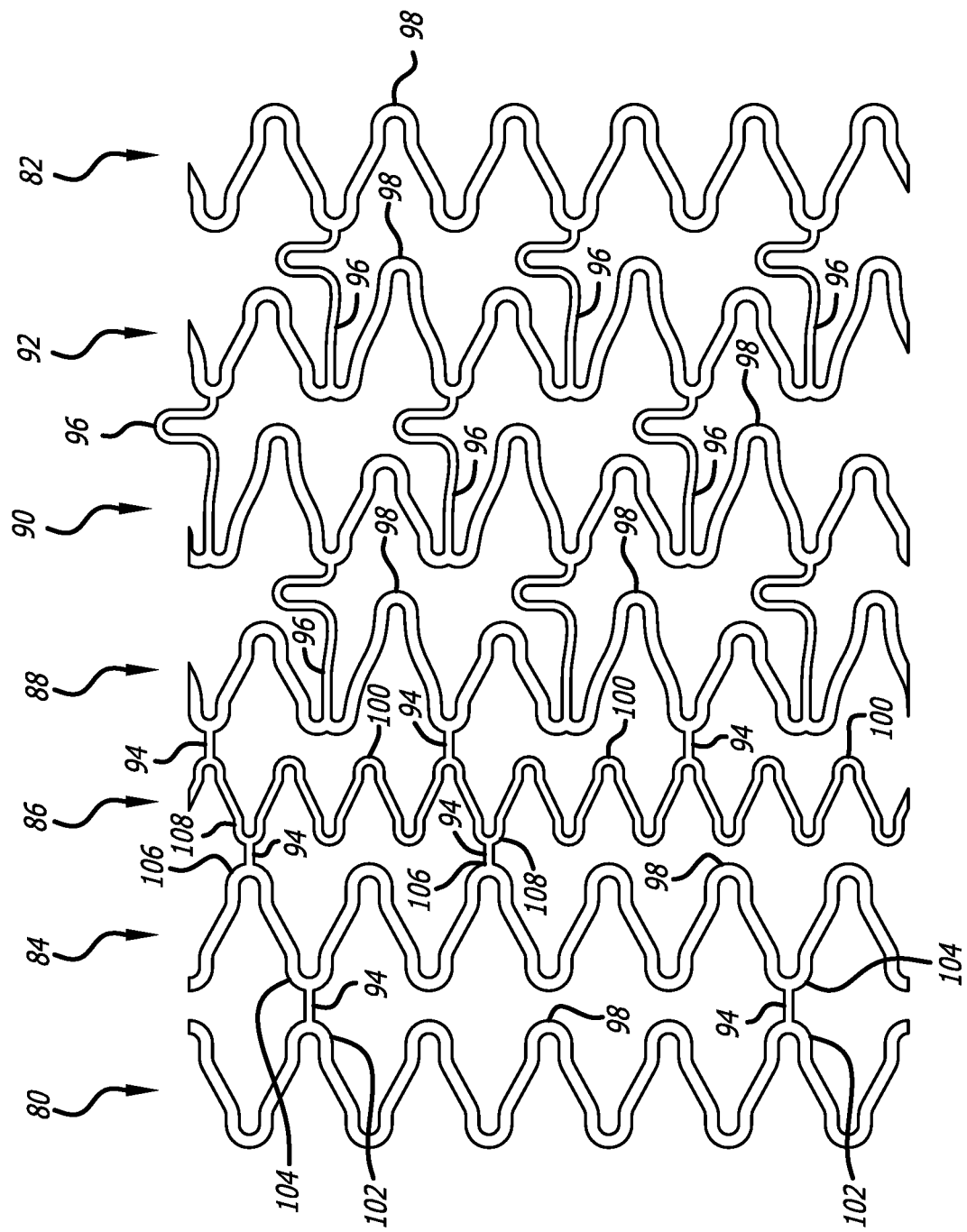

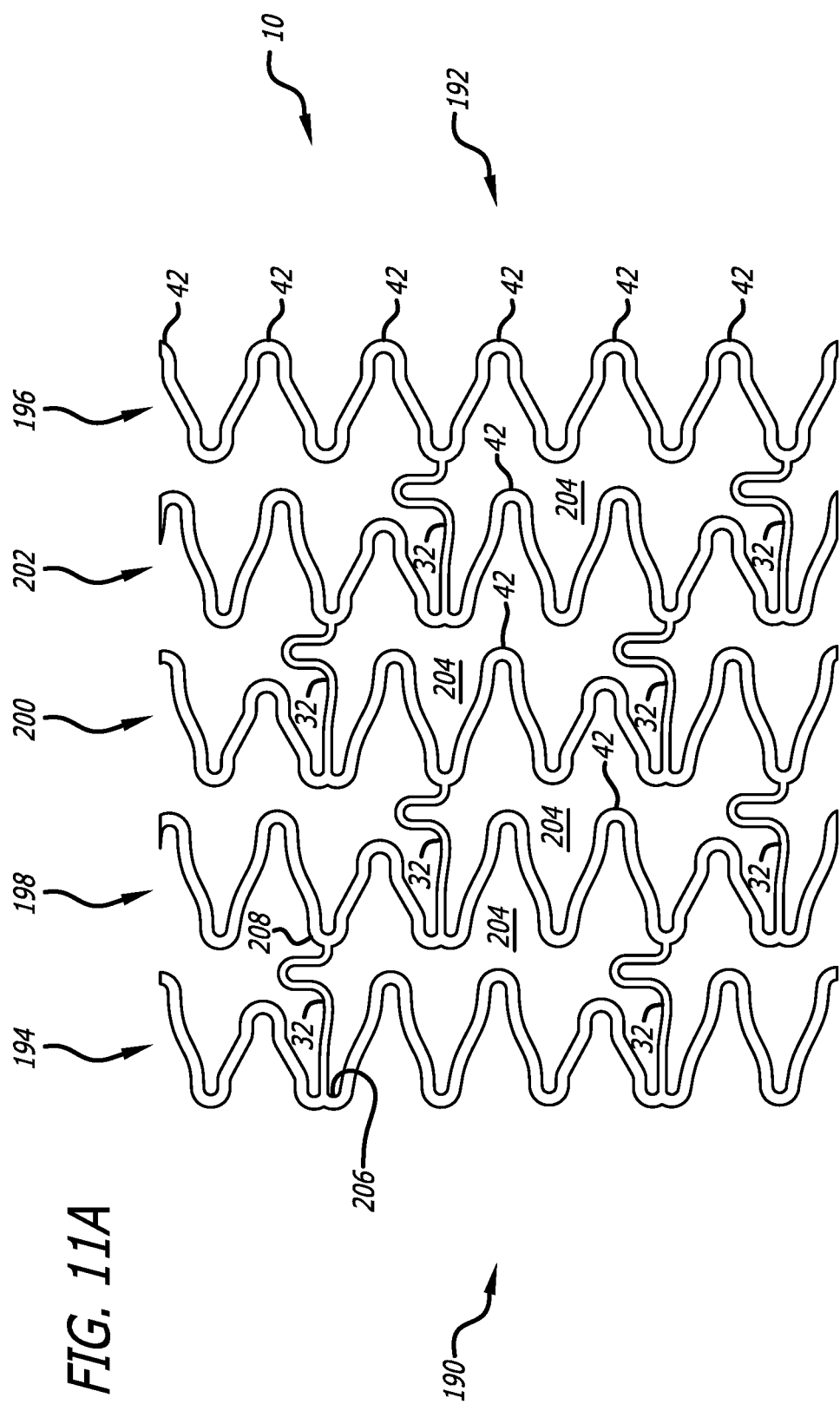

INTRAVASCULAR STENT

BACKGROUND

The present invention relates to expandable endoprosthesis devices, generally known as stents, which are designed for implantation in a patient's body lumen, such as a blood vessel to maintain the patency thereof. These devices are particularly useful in the treatment and repair of blood vessels after a stenosis has been compressed by percutaneous transluminal coronary angioplasty (PTCA) or percutaneous transluminal angioplasty (PTA) or removed by atherectomy or other means.

Stents are generally cylindrically-shaped devices which function to hold open and sometimes expand a segment of a blood vessel or other lumen such as a coronary artery. They are particularly suitable for use to support the lumen or hold back a dissected arterial lining which can occlude the fluid passageway therethrough.

A variety of devices are known in the art for use as stents and has included a plastically deformable wire mesh in a variety of patterns that is expanded after being placed intraluminally on a balloon catheter; helically wound coiled springs manufactured from an expandable heat sensitive metal; and self-expanding stents inserted in a compressed state and shaped in a zigzag pattern. One of the difficulties encountered using prior art stents involved maintaining the radial rigidity needed to hold open a body lumen while at the same time maintaining the longitudinal flexibility of the stent to facilitate its delivery and accommodate the often tortuous path of the body lumen. Other problems encountered by using prior art stents involve maintaining stent longitudinal flexibility and longitudinal stent compression. Some prior art stents are highly longitudinally flexible, however, these stents tend to experience higher longitudinal stent compression when the stent is subject to an axial load.

Another problem area for prior art stents has been the flexibility in the stent distal end. Many prior art stents have uniform longitudinal flexibility along their lengths. It may be desirable to have a stent with a higher degree of flexibility in the distal end to better track through tortuous calcified anatomy.

Another problem with prior art stents occurs when a first stent is deployed in a blood vessel, and the deployed stent blocks access to a side branch vessel which can reduce blood flow to the side branch vessel and block access for deployment of a second stent in the side branch vessel.

The devices disclosed herein overcome the deficiencies of the prior art devices and provide stents having a high degree of longitudinal flexibility, increased radial strength, enhanced side branch access, and improved longitudinal strength compression.

SUMMARY OF THE INVENTION

The present devices are directed to stents having enhanced longitudinal flexibility and high longitudinal strength compression. The stents have greater flexibility along their longitudinal axis to facilitate delivery through tortuous body lumens but remain highly stable and resistant to longitudinal compression incurred when another device tries to cross the deployed stent. The unique link patterns of the stents permit both greater longitudinal flexibility and higher longitudinal strength compression compared to prior art stents.

Each of the different embodiments of stents of the present invention includes a plurality of adjacent cylindrical rings which are generally expandable in the radial direction and arranged in alignment along a longitudinal stent axis. The cylindrical rings are formed in a serpentine wave pattern transverse to the longitudinal axis and contain a plurality of alternating peaks and valleys. At least one link extends between adjacent cylindrical rings and connects them to one another. These links insure minimal longitudinal contraction during radial expansion of the stent in the body vessel. The links can be positioned in differing configurations or patterns along the stent length to enhance stent retention on the delivery catheter, eliminate strut fractures, enhance longitudinal stent flexibility, and enhance longitudinal strength compression.

The resulting stent structures are a series of radially expandable cylindrical rings that are spaced longitudinally close enough so that small dissections in the wall of a body lumen may be pressed back into position against the lumenal wall, but not so close as to compromise the longitudinal flexibility of the stent both when being negotiated through the body lumens in their unexpanded state and when expanded into position. The serpentine patterns allow for an even expansion around the circumference by accounting for the relative differences in stress created by the radial expansion of the cylindrical rings.

Each of the stents of the present invention can be readily delivered to the desired lumenal location by mounting it on an inflatable member, such as a balloon of a delivery catheter, and passing the catheter-stent assembly through the body lumen to the implantation site. A variety of means for securing the stent to the inflatable member of the catheter for delivery to the desired location is available. It is presently preferred to compress or crimp the stent onto the uninflated balloon in a known manner.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in sections, depicting a stent mounted on a delivery catheter disposed within a vessel.

FIG. 2 is an elevational view, partially in section, similar to the stent of FIG. 1 wherein the stent is expanded within a vessel.

FIG. 3 is an elevational view, partially in section, showing the stent of FIG. 1 expanded within the vessel after withdrawal of the delivery catheter.

FIG. 7A is a plan view depicting one embodiment of the stent in a flattened configuration and illustrating the connecting link pattern between the end rings and the body rings.

FIG. 11A is a plan view depicting one embodiment of the stent in a flattened configuration and illustrating the connecting link pattern between the end rings and the body rings.

DETAILED DESCRIPTION OF THE PREFERRED EMBODIMENTS

Figure 4A:
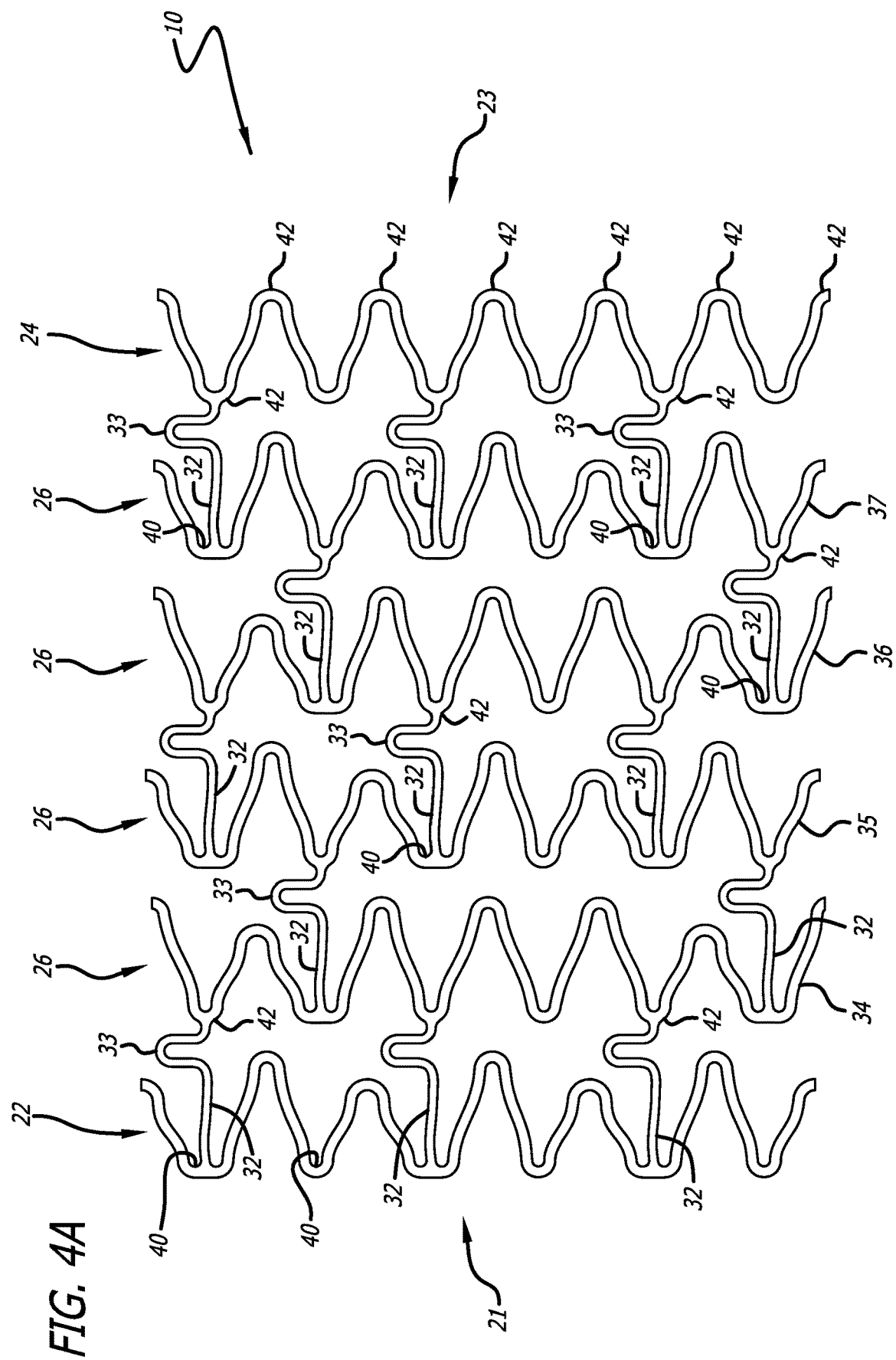
FIG. 4A is a plan view depicting one embodiment of the stent in a flattened configuration and illustrating the connecting link pattern between the end rings and the body rings.

Prior art stent designs, such as the MULTILINK STENT® manufactured by Abbott Cardiovascular Systems, Inc., Santa Clara, Calif., include plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical ring. A more detailed discussion of the configuration of the MULTILINK STENT® can be found in U.S. Pat. No. 5,569,295 (Lam) and U.S. Pat. No. 5,514,154 (Lau et al.), whose contents are hereby incorporated by reference.

One embodiment of the present stent is shown in FIG. 1, where stent 10 is mounted onto delivery catheter 11. Stent 10 generally includes a plurality of radially expandable cylindrical ring 12 disposed generally coaxially and interconnected by links 13 disposed between adjacent cylindrical ring 12. The delivery catheter 11 has an inflatable portion or balloon 14 for expanding stent 10 within artery 15 or other vessels.

The delivery catheter 11 onto which stent 10 is mounted is similar to a conventional balloon dilatation catheter for angioplasty procedures. The balloon 14 may be formed of suitable materials such as polyethylene, polyethylene terephthalate, polyvinyl chloride, nylon, and ionomers such as SURLYN® manufactured by the Polymer Products Division of the DuPont Company. Other polymers also may be used.

In order for stent 10 to remain in place on balloon 14 during delivery to the artery 15, stent 10 is compressed or crimped onto balloon 14.

The delivery of stent 10 to a coronary artery, for example, is accomplished in the following manner. Stent 10 is first mounted onto inflatable balloon 14 on the distal extremity of delivery catheter 11. Stent 10 may be crimped down onto balloon 14 to obtain a low profile. The catheter-stent assembly can be introduced within the patient's vasculature in a conventional technique through a guiding catheter (not shown). Guidewire 18 is disposed through the arterial section. The catheter-stent assembly is then advanced over guidewire 18 within artery 15. Balloon 14 of catheter 11 is inflated to expand stent 10 against the inside of artery 15, which is illustrated in FIG. 2. While not shown in the drawing, artery 15 is preferably over expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid therethrough.

In general, stent 10 serves to hold open artery 15 after catheter 11 is withdrawn, as illustrated in FIG. 3. Due to the formation of stent 10 from an elongated tubular member, the undulating component of the cylindrical elements of stent 10 is relatively flat in a transverse cross-section so that when stent 10 is expanded, cylindrical ring 12 are pressed into the wall of artery 15. Cylindrical ring 12 of stent 10 that are pressed into the wall of artery 15 will eventually be covered with endothelial cell growth that further minimizes blood flow turbulence. The serpentine pattern of cylindrical rings 12 provides good tacking characteristics to prevent stent movement within the artery.

Figure 4B:
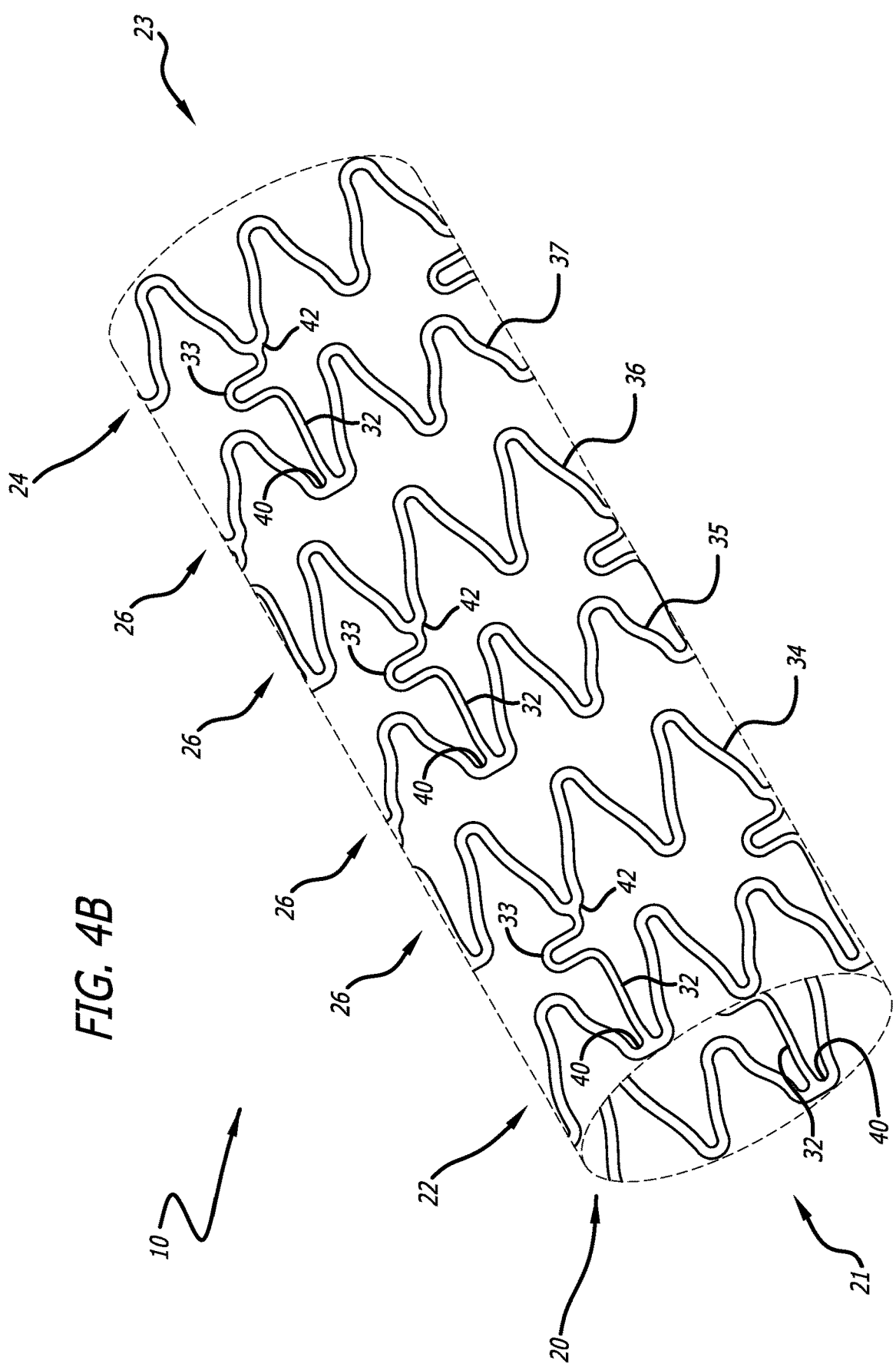
FIG. 4B is a perspective view of the stent of FIG. 4A in a tubular configuration.

In one embodiment, shown in FIGS. 4A and 4B, stent 10 includes a tubular body 20 having a distal end ring 22 and a proximal end ring 24. A number of body rings 26 are positioned between the distal end ring 22 and the proximal end ring 24. When the stent is expanded, the stent length, after expansion, remains substantially the same as that prior to expansion, which is desirable for positioning the stent at a precise location in artery 15. By maintaining the overall stent length during expansion, there is minimal trauma or injury to the artery in the axial direction from the radial expansion of the stent rings.

In the FIGS. 4A, 4B embodiment, all of the rings are positioned in an in-phase relationship and are connected by links 32. The tubular body 20 has a distal end 21 and a proximal end 23. The distal end ring 22 is connected to the first body ring 34 by three links 32. The links extend from a valley 40 of the distal end ring 22 to a peak 42 of the first body ring 34. As used herein, the term "peak" is interchangeable with the term "crest." The end rings 22, 24 and the body rings 26 are connected by links 32 having a pattern of 3 links-2 links-3 links along the length of the stent. The distal end ring 22 is connected to the first body ring 34 by three links 32; the first body ring 34 is connected to the second body ring 35 by two links 32; the second body ring 35 is connected to the third body ring 36 by three links 32; the third body ring 36 is connected to the fourth body ring 37 by two links; and the proximal end ring 24 is connected to the fourth body ring 37 by three links 32. The alternating pattern of 3-2-3-2-3 links provides increased longitudinal stent flexibility useful in delivering the crimped stent system to the treatment site while maintaining good longitudinal strength resistance for the deployed (i.e. expanded) stent in the blood vessel due to axial forces on the stent which may occur, post-deployment, due to interaction with other devices (e.g. secondary stent systems, imaging catheters, balloon dilatation systems, etc) which are also transited within the tortuous body lumens. As an alternative embodiment, a link pattern of 3-2-3-2-3-2-3-3 provides a more stable ring configuration at the proximal end of the stent where the last two rings are connected by three links.

Figure 5A:
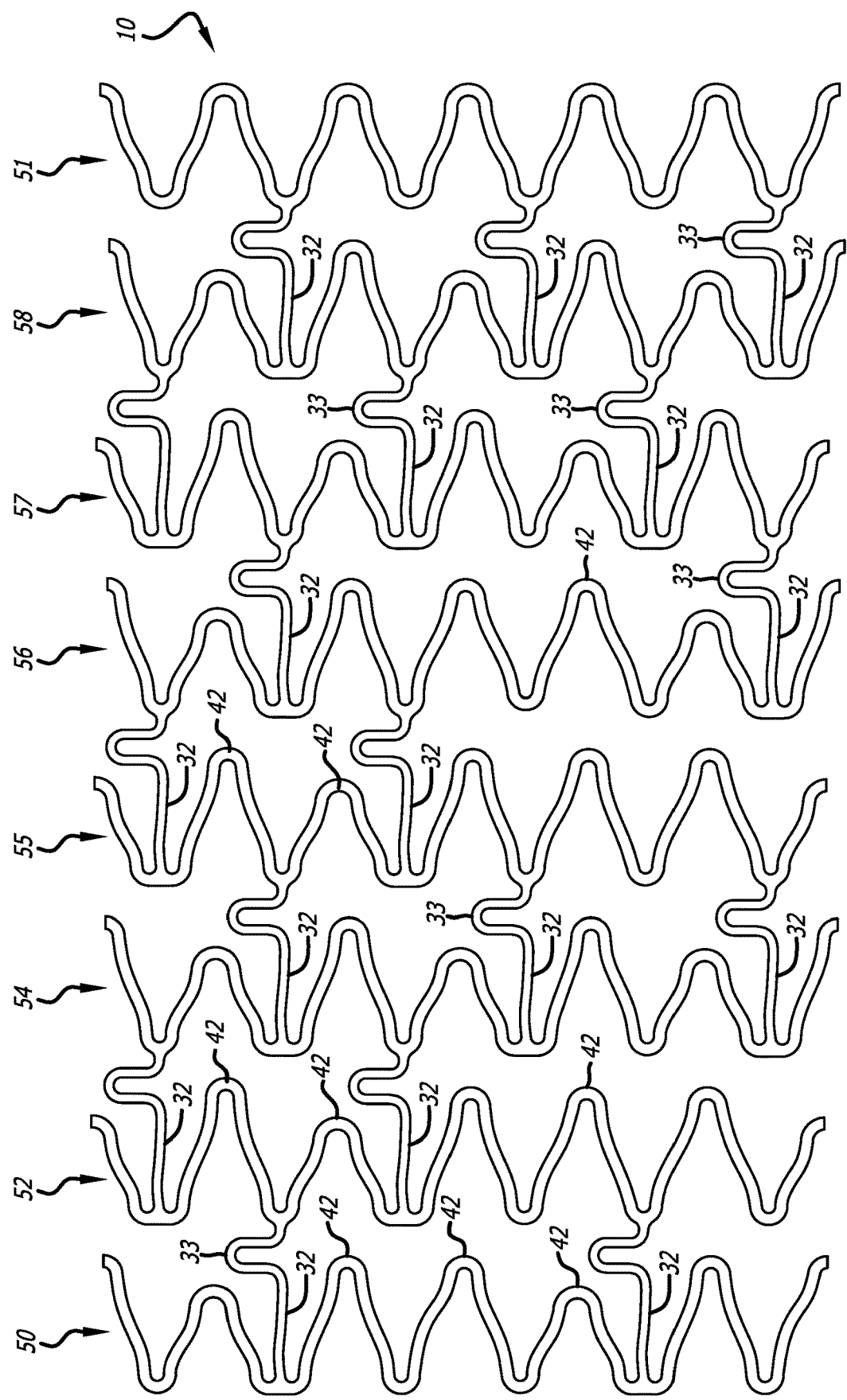
FIG. 5A is a plan view depicting one embodiment of the stent in a flattened configuration and illustrating the connecting link pattern between the end rings and the body rings.
Figure 5B:
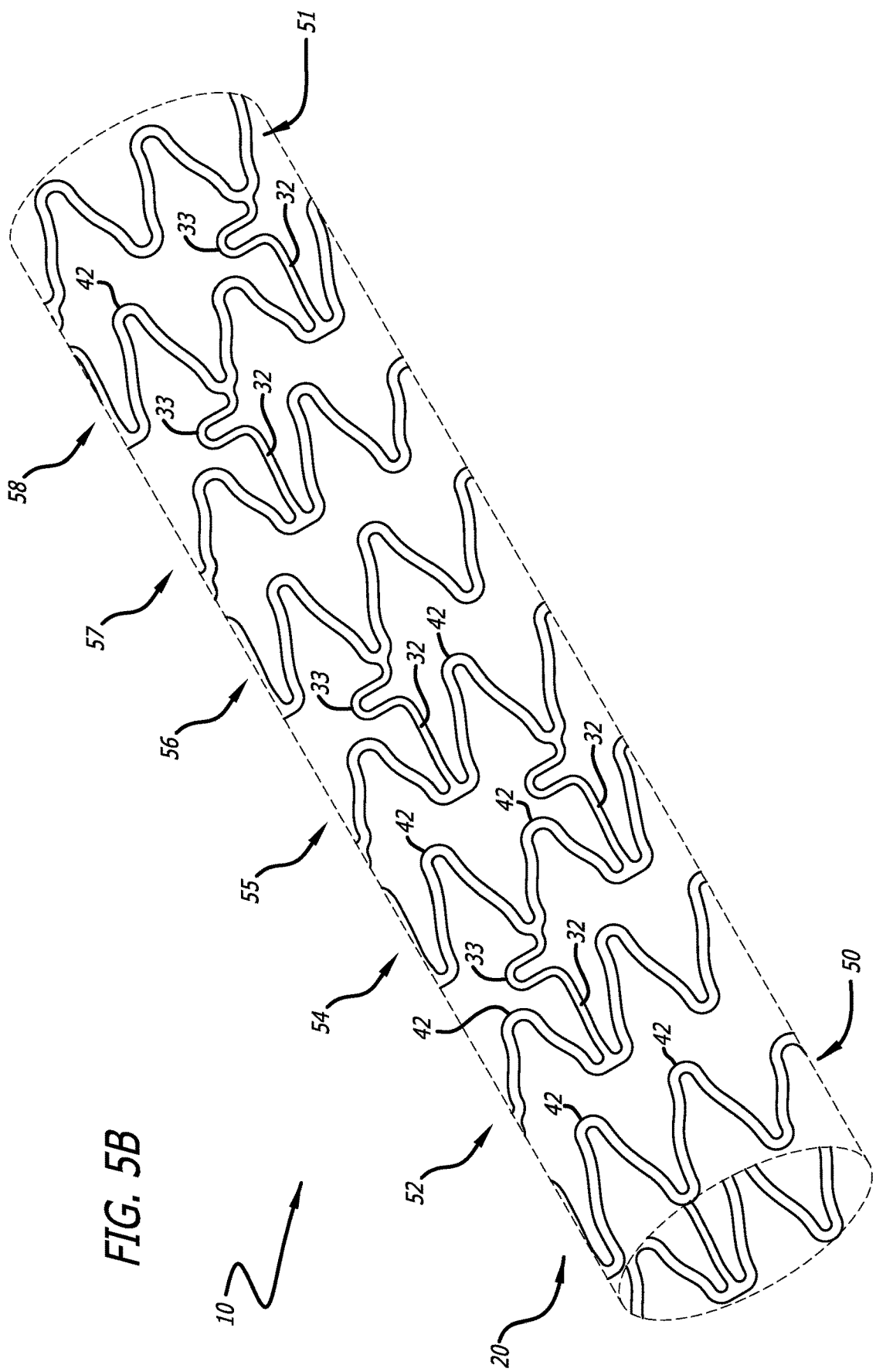
FIG. 5B is a perspective view of the stent of FIG. 5A in a tubular configuration.

In another embodiment, as shown in FIGS. 5A and 5B, the tubular body 20 includes a distal end ring 50 and a proximal end ring 51 and a plurality of body rings therebetween. The tubular body has a compressed (or crimped) diameter and an expanded implanted diameter. The end rings and the body rings are positioned in an in-phase relationship. The end rings and the body rings are connected by an alternating pattern of 2 links-2 links-3 links-2 links-2 links-3 links. The distal end ring 50 is connected to the first body ring 52 by two links 32; the first body ring 52 is connected to the second body ring 54 by two links 32; the second body ring 54 is connected to the third body ring 55 by three links 32; the third body ring 55 is connected to the fourth body ring 56 by two links 32; the fourth body ring 56 is connected to the fifth body ring 57 by two links 32; the fifth body ring 57 is connected to the sixth body ring 58 by three links 32; and the proximal end ring 51 is connected to the sixth body ring 58 by three links 32. The flexibility of the stent also is affected by the spacing of the links circumferentially around tubular body 20. For example, referring to FIG. 5A, each of the rings has six peaks 42, and the links 32 are separated by three peaks 42 on the distal end ring 50. The two links 32 between first body ring 52 and second body ring 54 are separated by two peaks 42 in one circumferential direction and four peaks in the opposite circumferential direction. The three links 32 connecting the second body ring 54 to the third body ring 54 body ring are separated by two peaks 42. The tubular body 20 has a compressed diameter and an expanded implanted diameter. There are some advantages to the link pattern shown in FIGS. 5A, 5B. With two adjacent links 32 being separated by only two peaks 42 between some adjacent body rings, there is more stability longitudinally but potentially less flexibility in bending. In other words, when two adjacent links are separated by three or four peaks, each link is under greater stress during bending than if two links were closer together. Accordingly, the preferred link pattern as disclosed provides good bending fatigue durability, high flexibility and provides greater space between struts of the stent which aids in providing improved stent securement on the balloon. The stent of FIGS. 5A, 5B also provides high longitudinal strength compression. As an alternative embodiment, a link pattern of 3-2-3-2-3-2-3-3 provides a more stable ring configuration at the proximal end of the stent where the last two rings are connected by three links.

Figure 6A:
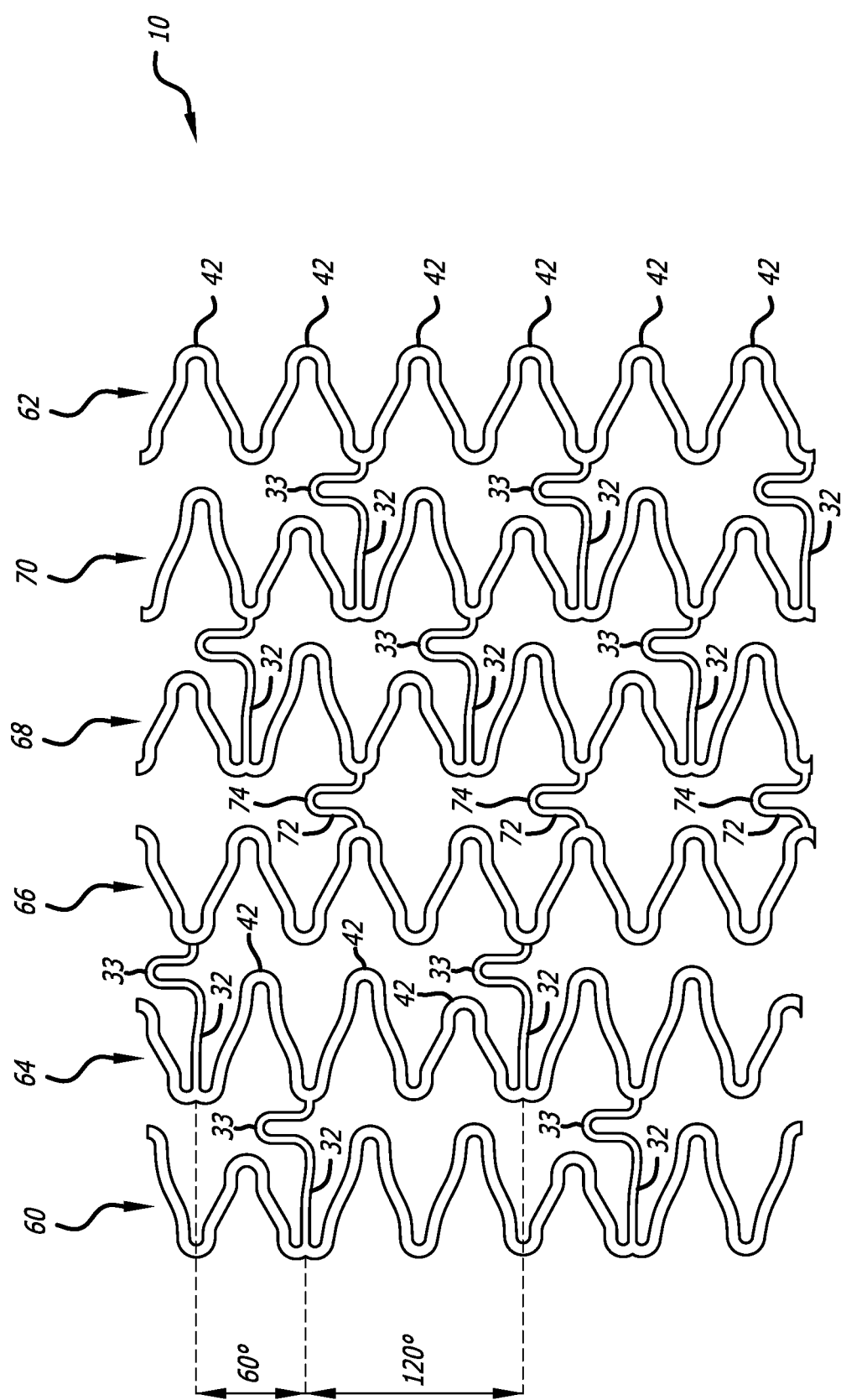
FIG. 6A is a plan view depicting one embodiment of the stent in a flattened configuration and illustrating the connecting link pattern between the end rings and the body rings.
Figure 6B:
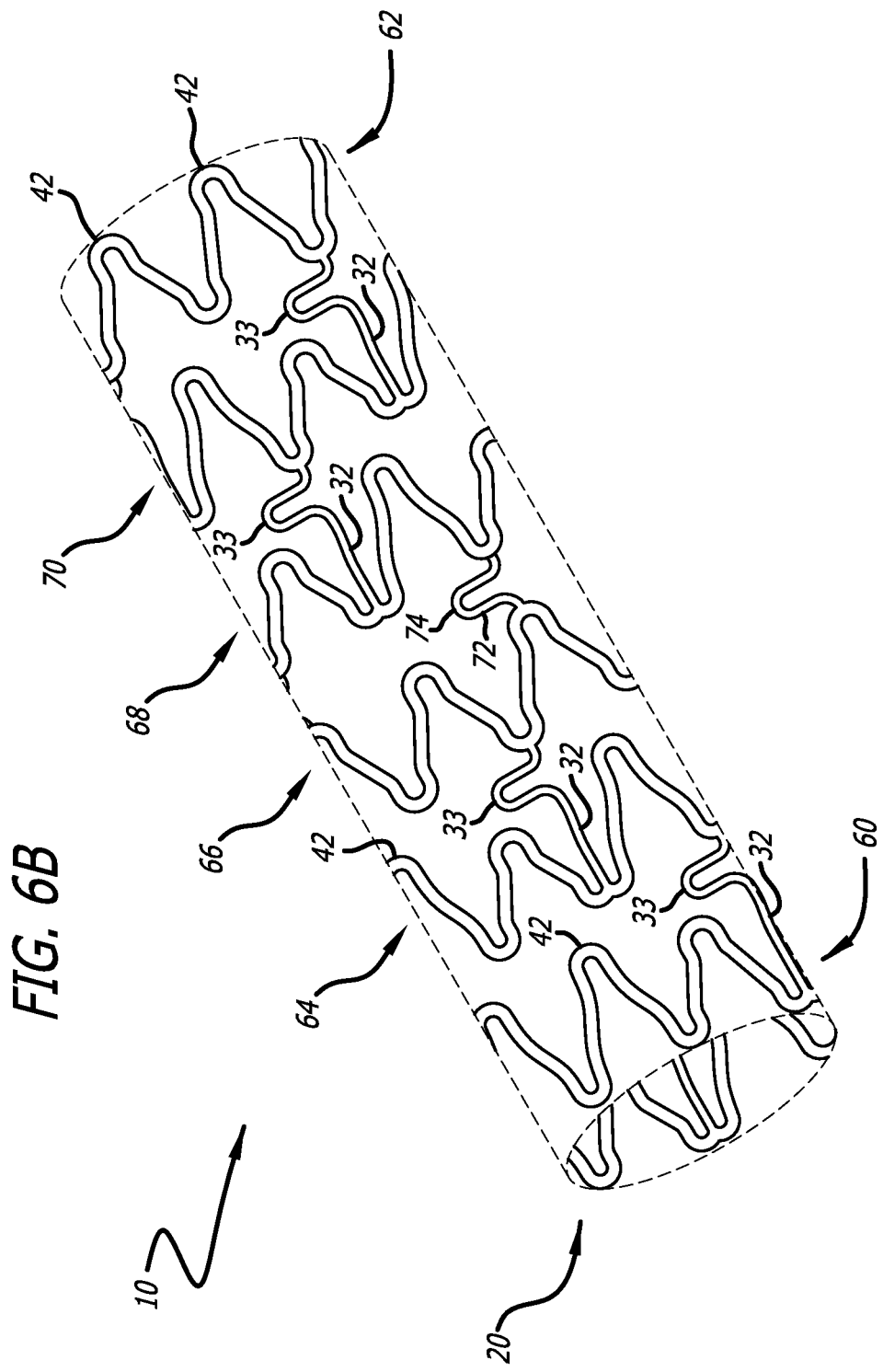
FIG. 6B is a perspective view of the stent of FIG. 6A in a tubular configuration.

In another embodiment, shown in FIGS. 6A and 6B, stent 10 includes a tubular body 20 comprised of a distal end ring 60, a proximal end ring 62, and body rings 64, 66, 68 and 70. There are six rings in this embodiment and each ring has six peaks 42. The tubular body 20 has a compressed diameter and an expanded implanted diameter. The distal end ring 60, first body ring 64, and second body ring 66 are positioned in an in-phase relationship, while the proximal end ring 62, third body ring 68, and fourth body ring 70 are positioned in an in-phase relationship. The second body ring 66 and third body ring 68 are positioned in an out-of-phase relationship. Two links 32 connect the distal end ring 60 to the first body ring 64, and two links 32 connect the first body ring 64 to the second body ring 66. Three links 72 connect the second body ring 66 to the third body ring 68. The three links 72 have a curved portion 74 and no linear portions to connect with adjacent body rings 66, 68. Three links 32 connect the third body ring 68 to the fourth body ring 70. Three links 32 connect the fourth body ring 70 to the proximal end ring 62. In this embodiment, the link pattern 2-2-3-3-3 provides a highly flexible in the distal section for deliverability of the crimped stent, while still providing good longitudinal strength stability in the proximal end of the deployed/expanded stent. The proximal end of the deployed/expanded stent is more often the region in which undesired contact with secondary luminal devices occurs. Where the adjacent rings are connected by two links, there are three peaks 42 between links, which are positioned 180° apart along the circumference of the stent. The two links 32 connecting the distal end ring 60 and the first body ring 64 are circumferentially offset by 60° in one direction and 120° in the opposite direction from the two links 32 connecting the first body ring 64 to the second body ring 66. This circumferential offset is critical to enhancing longitudinal flexibility while maintaining good longitudinal strength compression (i.e., axial compression loads).

In the stent embodiments shown in FIGS. 4A-6B, all of the connecting links 32 have non-linear links. The non-linear links have a curved portion 33 that is transverse to the stent longitudinal axis and acts as a hinge to allow the stent to flex and bend when being delivered through tortuous body lumens. The usage of a non-linear portion 33 may not be required in conditions in which the longitudinal flexibility is not required. Often in rings connected only with two links, the non-linear portion is not required depending of the needed flexibility of the compressed (i.e., crimped) stent on a delivery system.

Figure 7B:
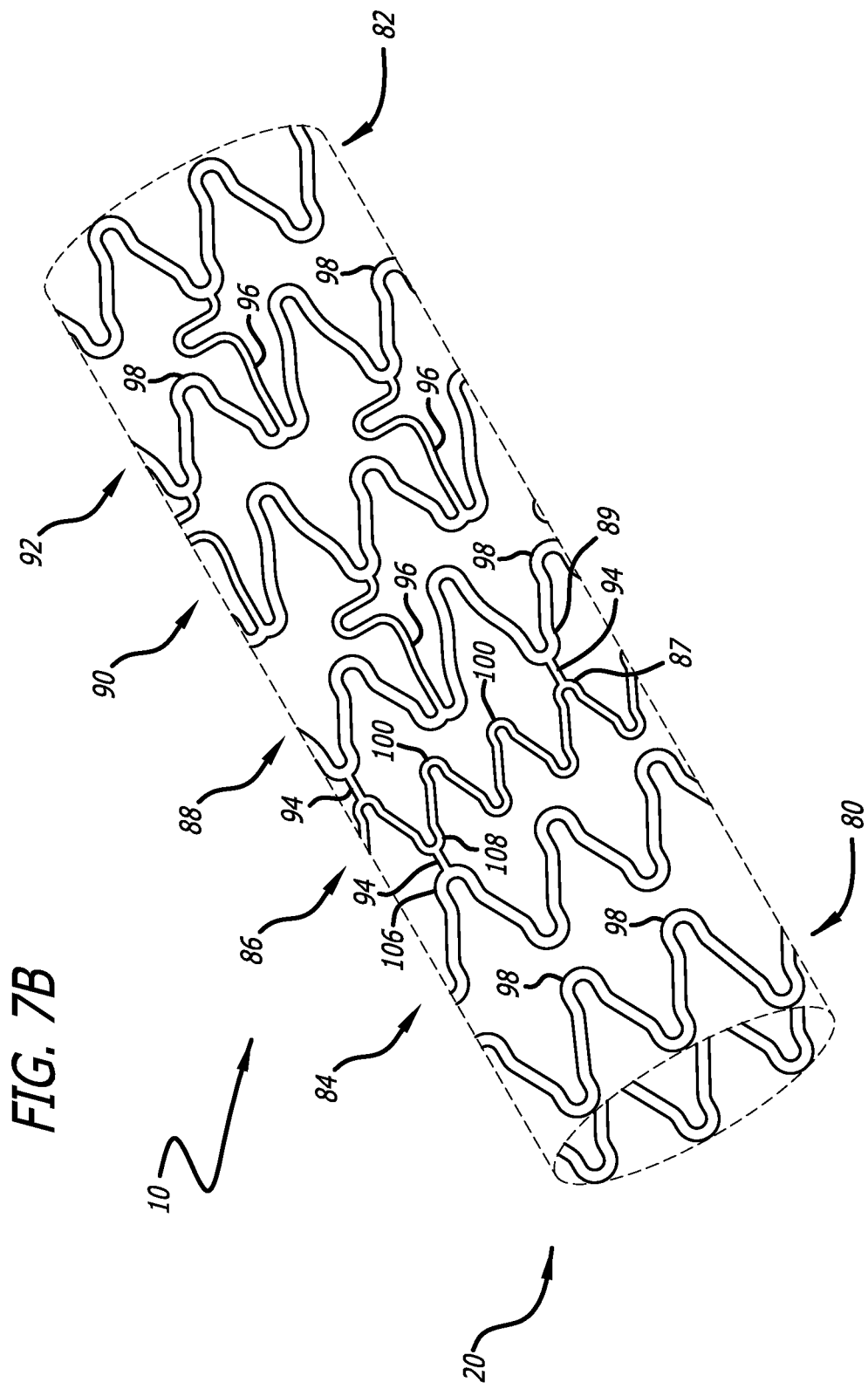
FIG. 7B is a perspective view of the stent of FIG. 7A in a tubular configuration.

In another embodiment, shown in FIGS. 7A and 7B, stent 10 includes a tubular body 20 comprised of a distal end ring 80, a proximal end ring 82, and body rings 84-92. The tubular body 20 has a compressed diameter and an expanded implanted diameter. There are seven rings in this embodiment, and they are arranged to provide maximum flexibility and deliverability, as well as having improved longitudinal strength compression. The distal end ring 80 is connected to the first body ring 84 by two linear links 94 that extend from a peak 102 on the distal end ring 80 to an adjacent peak 104 on the first body ring 84. The distal end ring 80 and the first body ring 84 have six peaks or crests 98 and are in an out-of-phase relationship. The first body ring 84 is connected to the second body ring 86 by two linear links 94, which extend from a peak 106 on the first body ring 84 to an adjacent peak 108 on the second body ring 86. The second body ring 86 has nine peaks or crests 100. The first body ring 84 and the second body ring 86 are in an out-of-phase relationship. The second body ring 86 is connected to the third body ring 88 by three linear links 94. The linear links 94 extend from a peak 87 on the second body ring 86 to an adjacent peak 89 on the third body ring 88. The second body ring 86 and the third body ring 88 are positioned in an out-of-phase relationship. The third body ring 88, the fourth body ring 90, the fifth body ring 92, and the proximal end ring 82 are positioned in an in-phase relationship. The third body ring 88 is connected to the fourth body ring 90, which is connected to the fifth body ring 92, which is connected to the proximal end ring 82, all being connected by three links 96. The second body ring 86 is also referred to as a transition ring since it transitions between an out-of-phase relationship and an in-phase relationship. The nine-crest 100 of the second body ring 86 is necessary so that the peaks and valleys align where the connecting links connect the peak of one body ring to the peak or valley of an adjacent body ring. It essentially is transitioning between the out-of-phase rings on the distal end of the stent and the in-phase rings on the proximal end of the stent. This configuration improves flexibility and deliverability within the critical distal portion of the stent system (crimped stent on a catheter) but provides high longitudinal strength stability in the body and proximal majority of the stent post deployment. This configuration also provides a smaller crimp profile for the distal portion of the stent. The tubular body 20 has a compressed diameter and an expanded implanted diameter.

Figure 8A:
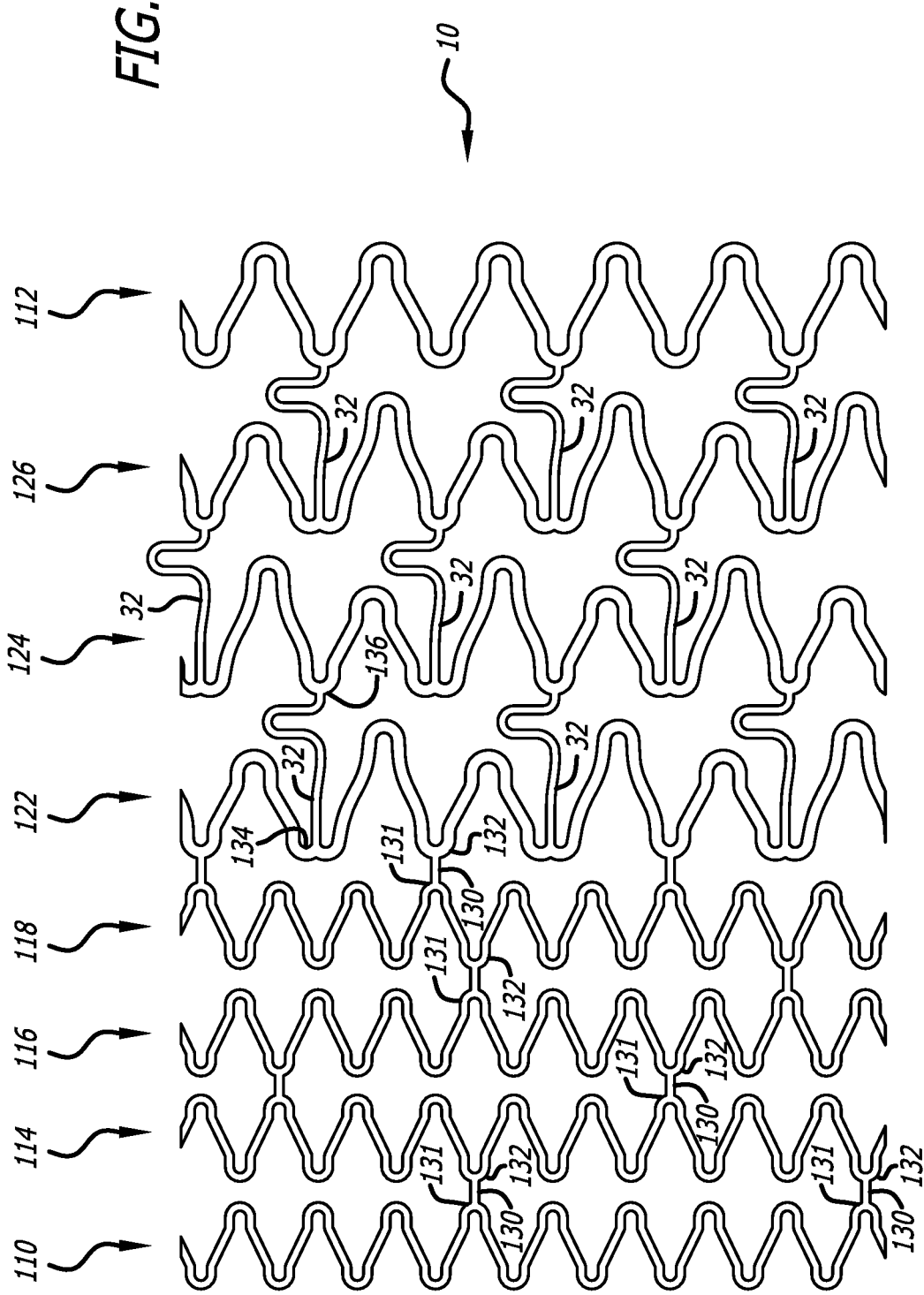
FIG. 8A is a plan view of one embodiment of the stent of the present invention in a flattened configuration and illustrating the connecting link pattern between the end rings and the body rings.
Figure 8B:
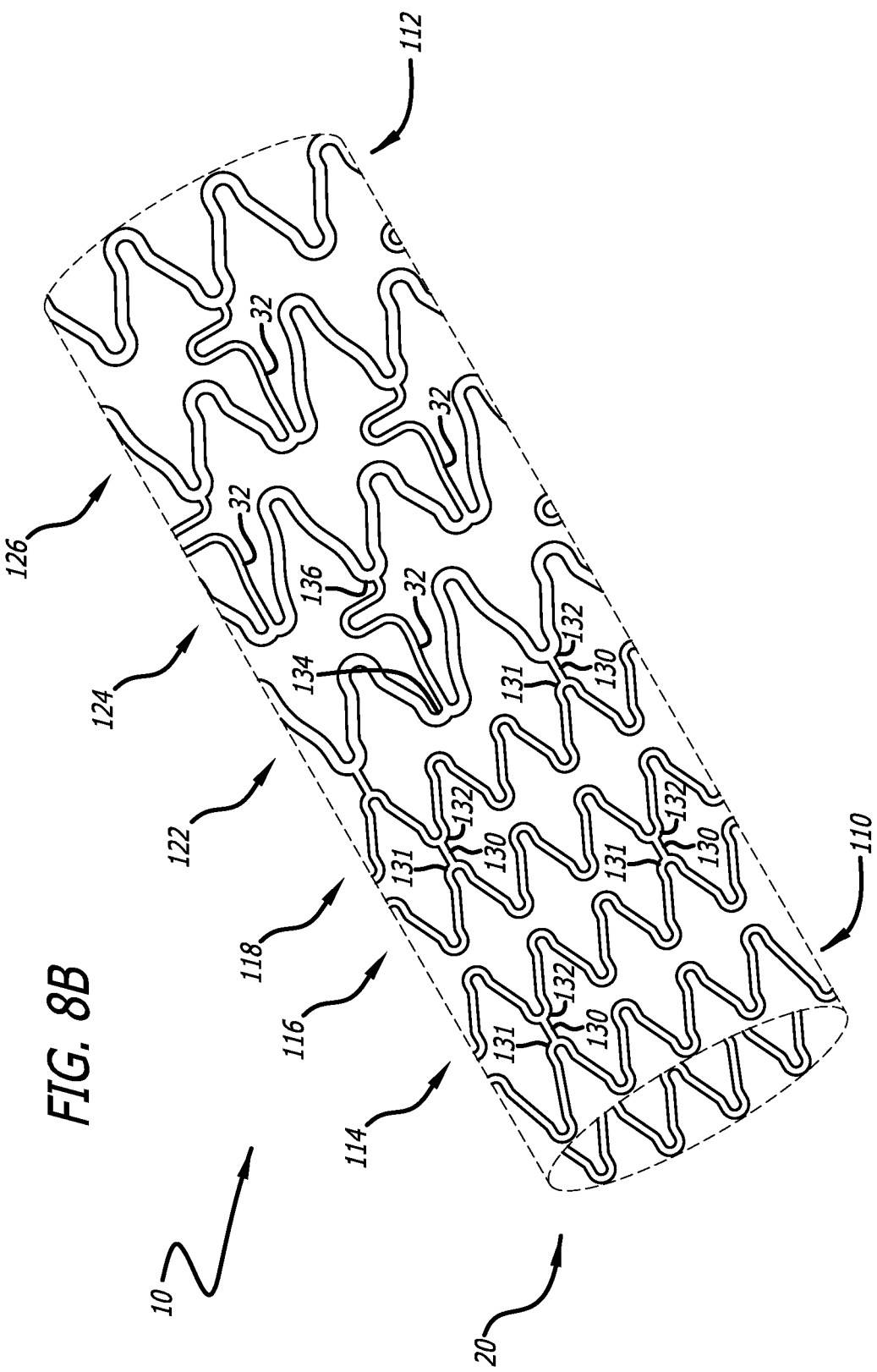
FIG. 8B is a perspective view of the stent of FIG. 8A in a tubular configuration.

In another embodiment, shown in FIGS. 8A and 8B, stent 10 includes a tubular body 20 comprised of a nine-crest distal end ring 110, a six-crest proximal end ring 112, and body rings 114, 116, 118, 122, 124 and 126. The tubular body 20 has a compressed diameter and an expanded implanted diameter. There are eight rings in this embodiment, four nine-crest rings on the distal portion and four six-crest rings on the proximal portion, and the rings are arranged to provide maximum flexibility and deliverability, as well as having improved longitudinal strength compression. The nine-crest distal end ring 110 is connected to the first nine-crest body ring 114 by two linear links 130 that extend from a first peak 131 on the distal end ring 110 to an adjacent second peak 132 on the first body ring 114. The first body ring 114 is connected to the second nine-crest body ring 116 by two linear links 130, which extend from a peak 131 on the first body ring 114 to an adjacent peak 132 on the second body ring 116. The second body ring 116 is connected to a third nine crest body ring 118 by two linear links 130. The linear links 130 extend from a peak 131 on the second body ring 116 to adjacent second peak 132 on the third body ring 118. The distal end ring 110, the first body ring 114, the second body ring 116, and the third body ring 118 are positioned in an out-of-phase relationship. The third body ring 118 is connected to a first six-crest body ring 122, which is connected to a second six-crest body ring 124, which is connected to a third six-crest body ring 126, which is connected to the six-crest proximal end ring 112, all being connected by three links 32. For the body rings 122, 124, 126 and proximal end ring 112, one end of the link 32 is connected to a valley 134 on one of the six-crest body rings, and the other end of the link is connected to a peak 136 on an adjacent six-crest body ring. The first six-crest body ring 122, the second six-crest body ring 124, the third six-crest body ring 126, and the six-crest proximal end ring 112 are positioned in an in-phase relationship. The third nine-crest body ring 118 is also referred to as a transition ring since it transitions between a nine-crest peak-to-peak out-of-phase relationship and the first six-crest body ring 122 in an out-of-phase relationship. This design allows for a 2 link configuration distally for deliverability with a more stable three link configuration proximally while not requiring a transition ring as per embodiment 7.

Figure 9A:
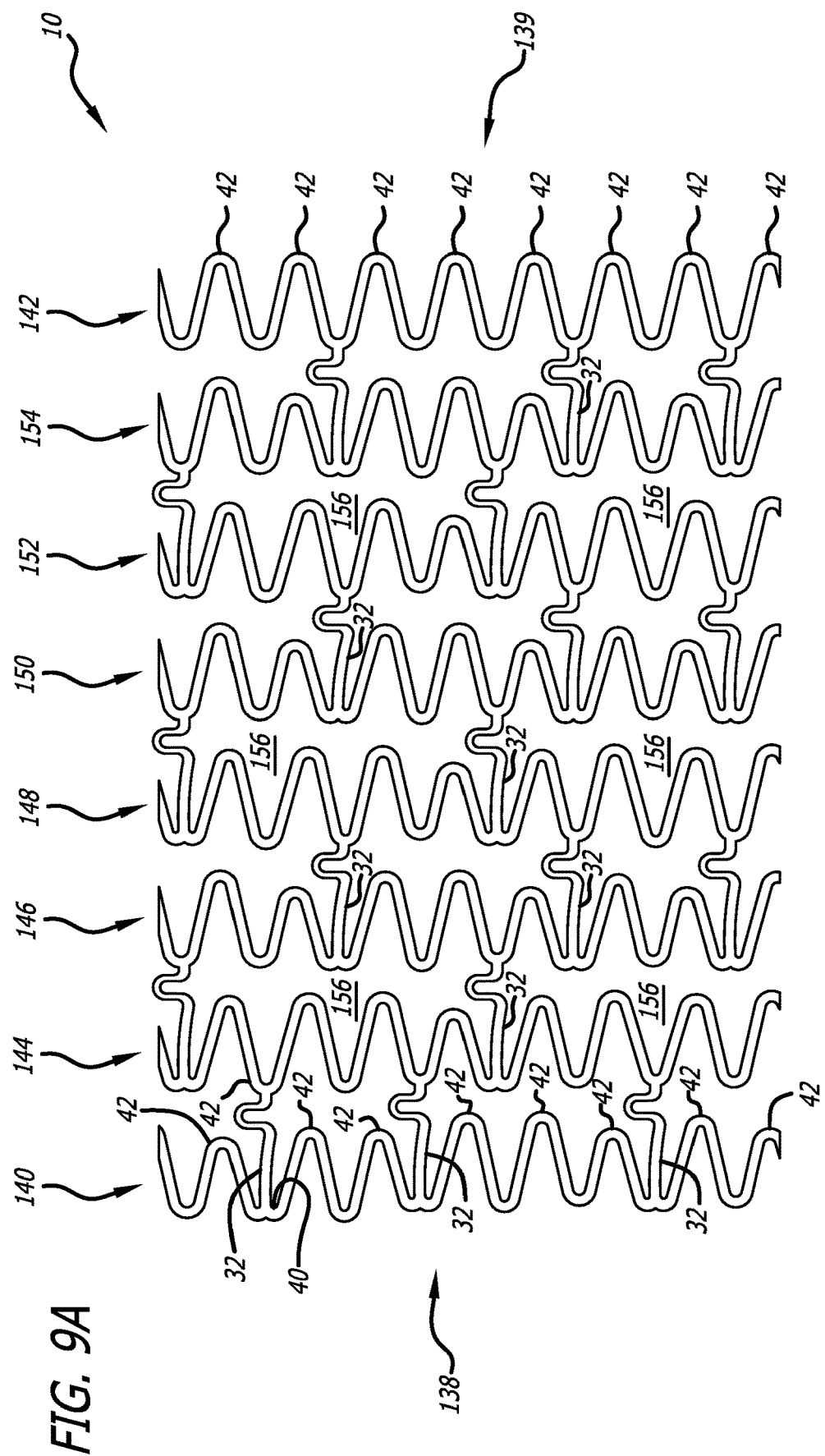
FIG. 9A is a plan view of one embodiment of the stent of the present invention in a flattened configuration and illustrating a portal for side branch vessel access.
Figure 9B:
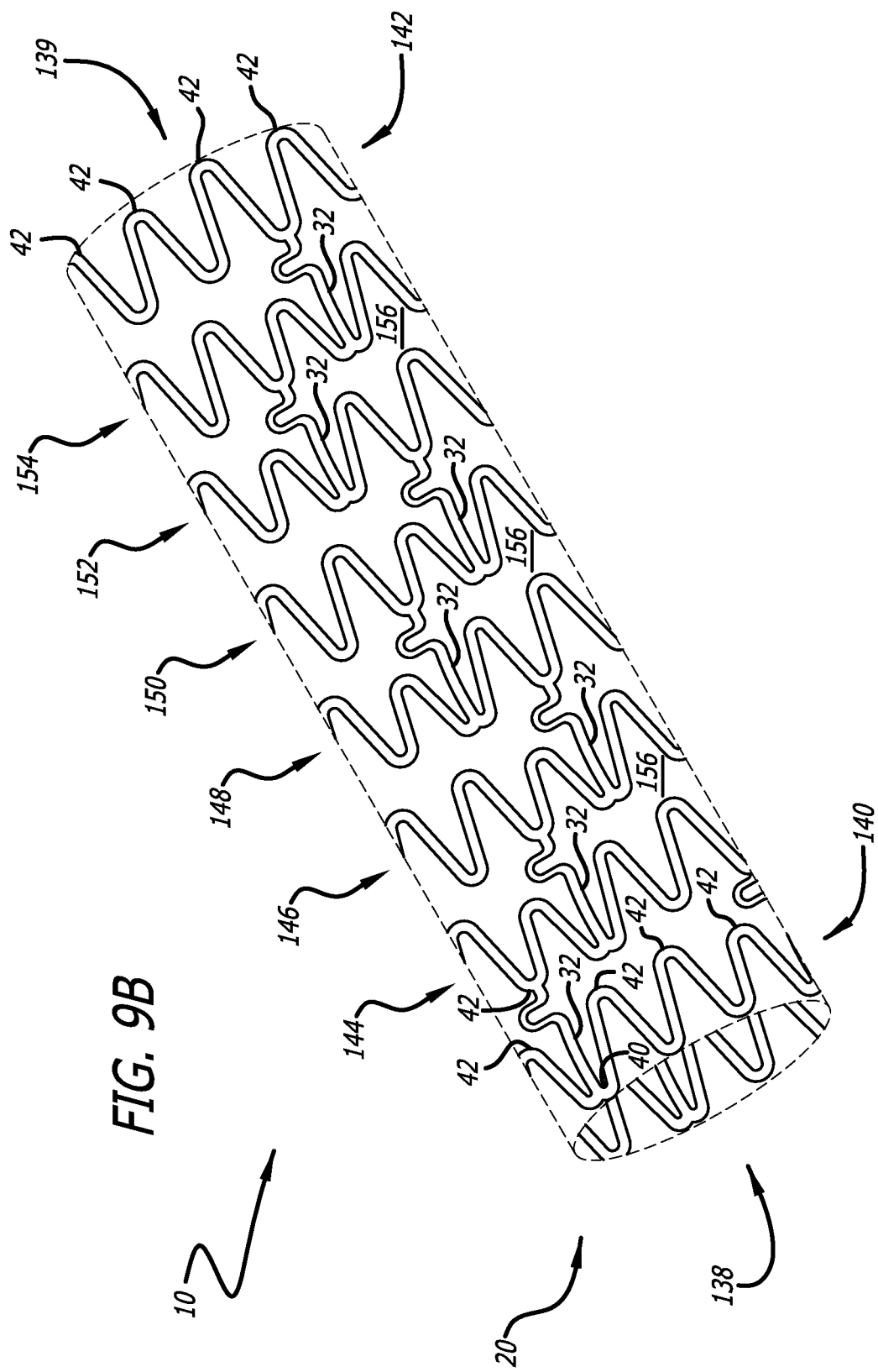
FIG. 9B is a perspective view of the stent of FIG. 9A in a tubular configuration.

In the FIGS. 9A and 9B embodiment, all of the rings are positioned in an in-phase relationship and are connected by links 32. The tubular body 20 has a compressed diameter and an expanded implanted diameter. The link configuration provides several portals for enhanced side branch vessel access as well as subsequent ability to enlarge the cell to a greater diameter opening using a secondary dilatation balloon. The tubular body 20 has a distal end 138 and a proximal end 139. The distal end ring 140 is connected to a first body ring 144 by three links 32. The links extend from a valley 40 of the distal end ring 140 to a peak 42 of the first body ring 144. The distal and proximal end rings 140, 142 and the body rings are connected by links 32 having a pattern of 3 links-2 links-3 links-2 links-3 links along the length of the stent. The distal end ring 140 is connected to the first body ring 144 by three links 32; the first body ring 144 is connected to a second body ring 146 by two links 32; the second body ring 146 is connected to a third body ring 148 by three links 32; the third body ring 148 is connected to the fourth body ring 150 by two links 32; the fourth body ring 150 is connected to the fifth body ring 152 by three links 32; the fifth body ring 152 is connected to the sixth body ring 154 by two links 32; and the proximal end ring 142 is connected to the sixth body ring 154 by three links 32. All of the rings have eight peaks or crests 42. The rings with three connecting links provide structure to the design to minimize any compression under longitudinal forces, while the rings with two connecting links reduce the chance of the side branch vessel being blocked by a link by one-third. The two-link rings can be referred to as portal rings (body rings 144, 146, 148, 150, 152 and 154). With portal rings, there is less of a need for precise positioning when implanting a stent in the main vessel and across a side branch vessel opening. If required, more rings connected by three links can be added to the distal end and the proximal end of the stent to provide more stability. The alternating 2-3-2-3 link pattern ensures that there is some ability to find an opening either distal or proximal to the initial cross location by probing one cell distal or proximal on a second effort to cross. In another similar embodiment (not shown), the alternating link pattern of the FIGS. 9A and 9B of 3-2-3-2-3 links, is changed to 3-2-3-2-3-3 to increase stability in the proximal section of the stent. Radiopaque markers can be placed on the stent or the delivery catheter corresponding to the portal rings and larger cell openings to better visualize placement of the secondary catheter into the side branch vessel.

In FIGS. 9A, 9B, the cells or portals 156 with only two links 32 increase the maximum size of the possible opening for side branch vessel access. There are four peaks or crests 42 in between each pair of links 32 providing maximum cell size. The maximum size of the opening (cells 156) is related to the path length of the cell 156 divided by pi and is referred to herein as the maximum side branch access diameter (MCSBA). The cells or portals 156 are big enough, when expanded, to permit access by a catheter or a stent system for treating the side branch vessel for an angioplasty, stenting, or some other procedure. Although the stent design in the embodiment in FIGS. 9A, 9B is an eight peak/crest 42 design, this concept can be applied to stent designs with different numbers of peaks/crests and rings, e.g., nine-crest three-link alternating with nine-crest two-link patterns.

Figure 10A:
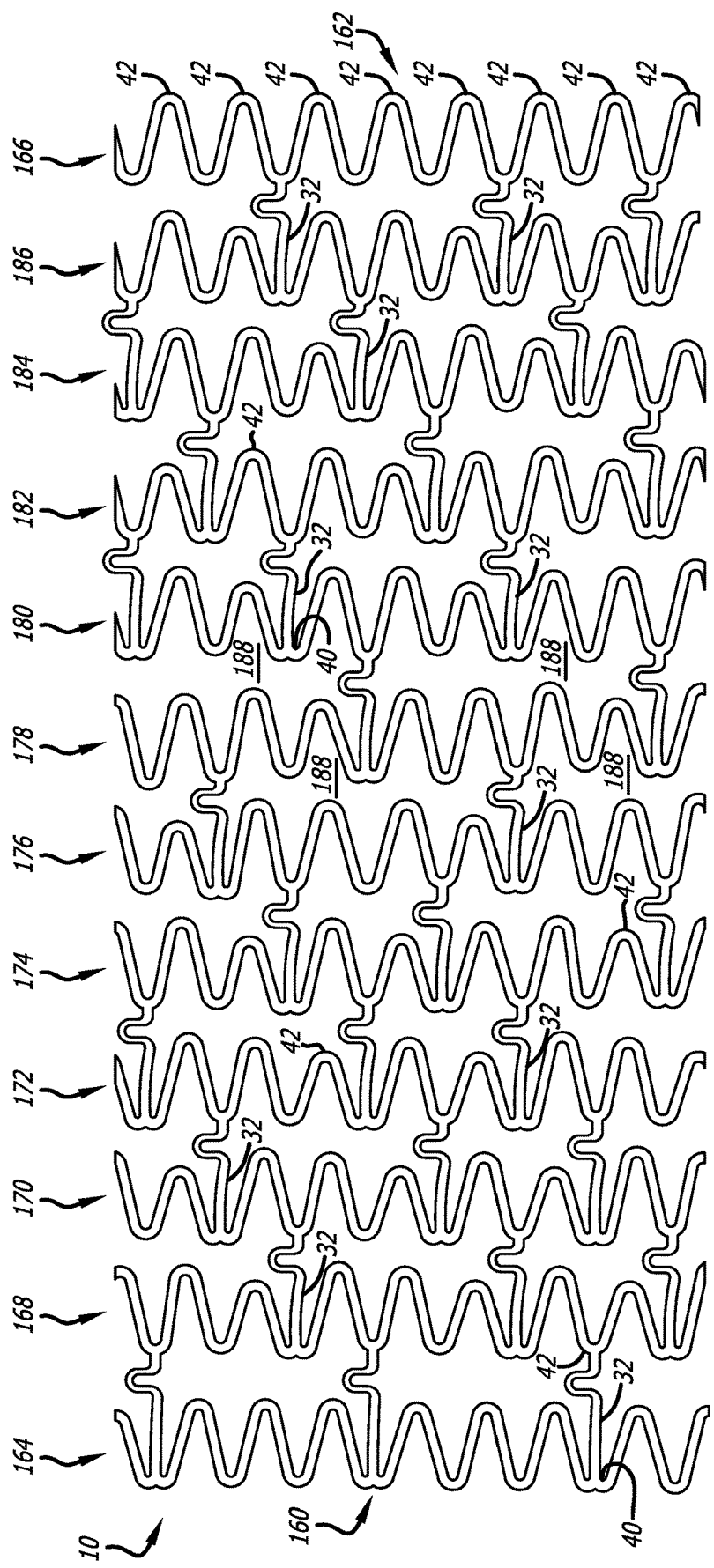
FIG. 10A is a plan view depicting one embodiment of the stent in a flattened configuration and illustrating the connecting link pattern between the end rings and the body rings.
Figure 10B:
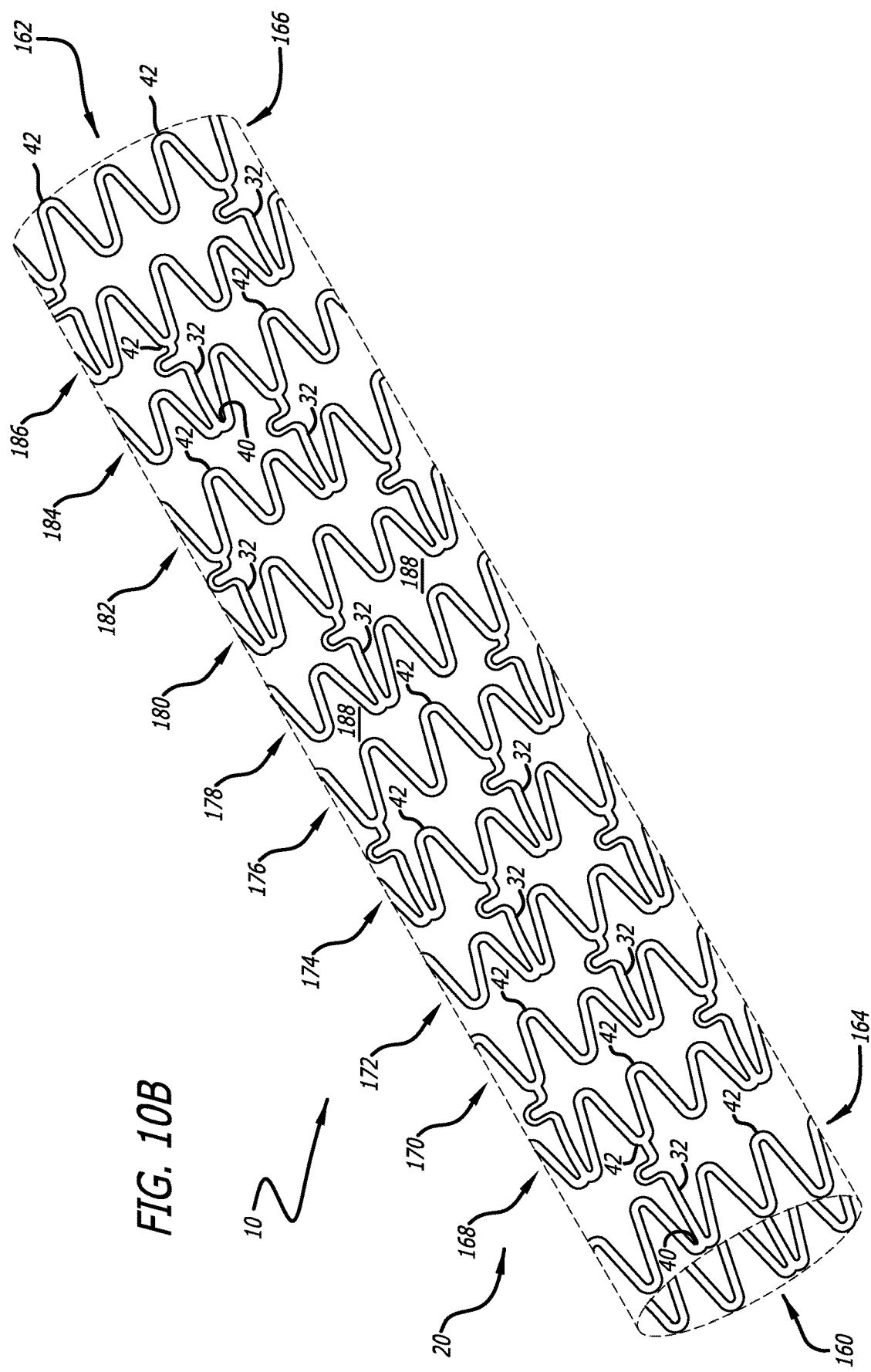
FIG. 10B is a perspective view of the stent of FIG. 10A in a tubular configuration.
Figure 11B:
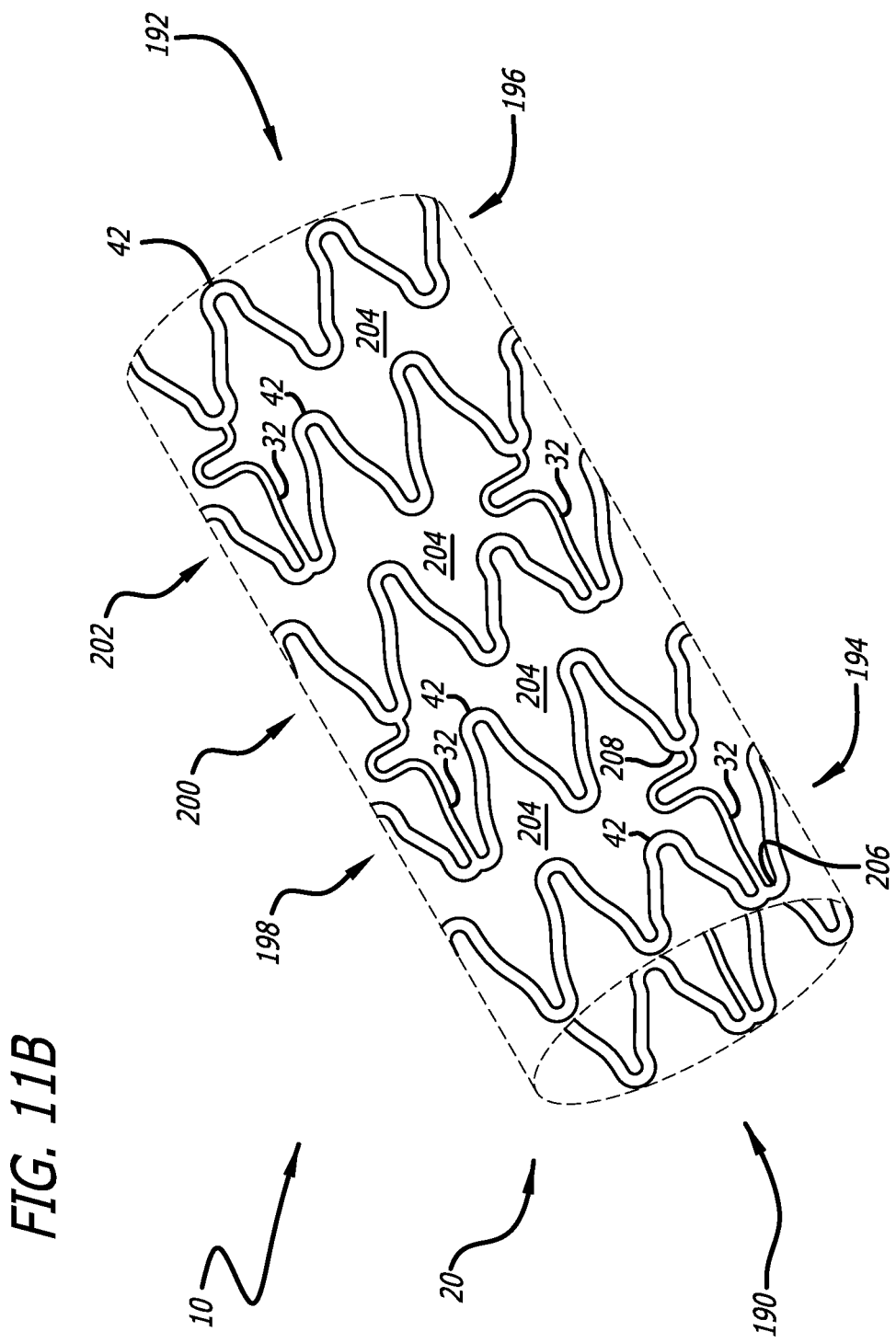
FIG. 11B is a perspective view of the stent of FIG. 11A in a tubular configuration.

In the FIGS. 10A and 10B embodiment, the stent 10 has twelve eight-crest (or peaks) rings 42 that are positioned in an in-phase relationship and are connected by links 32. The tubular body 20 has a compressed diameter and an expanded implanted diameter. The link configuration in the middle section of the stent provides several portals for enhanced side branch vessel access. The tubular body 20 has a distal end 160 and a proximal end 162. A distal end ring 164 is connected to the first body ring 168 by three links 32. The links extend from a valley 40 of the distal end ring 164 to a peak 42 of the first body ring 168. The first body ring 168 is connected to the second body ring 170 by three links 32; the second body ring 170 is connected to the third body ring 172 by three links 32; the third body ring 172 is connected to the fourth body ring 174 by three links 32; the fourth body ring 174 is connected to the fifth body ring 176 by three links 32; the fifth body ring 176 is connected to the sixth body ring 178 by two links 32; the sixth body ring 178 is connected to the seventh body ring 180 by two links 32; the seventh body ring 180 is connected to the eighth body ring 182 by three links 32; the eighth body ring 182 is connected to the ninth body ring 184 by three links 32; the ninth body ring 184 is connected to the tenth body ring 186 by three links 32; and the proximal end ring 166 is connected to the tenth body ring 186 by three links 32. All of the rings have eight peaks or crests 42. The rings with three connecting links 32 provide structure to the design to minimize any compression under longitudinal forces, while the rings with two connecting links reduce the chance of the side branch vessel being blocked by a link by one-third. The two link rings can be referred to as portal rings. With portal rings, there is less of a need for precise positioning when implanting a stent in the main vessel and across a side branch vessel opening. If required, more rings connected by three links can be added to the distal end and the proximal end of the stent.

In FIGS. 10A, 10B, cells or portals 188 with only two links 32 increase the maximum size of the possible opening for side branch vessel access. There are four peaks or crests 42 in between each pair of links 32 providing maximum cell size. The maximum size of the opening (cells 188) is related to the path length of the cell 188 divided by pi and provides the maximum circular side branch access diameter (MCSBAD). The cells or portals 188 are big enough, when expanded, to permit access by a catheter or a stent system for treating the side branch vessel for an angioplasty, stenting, or some other procedure. Although the stent design in the embodiment in FIGS. 10A, 10B is an eight-peak/crest 42 design, this concept can be applied to stent designs with different numbers of peaks/crests and rings, e.g., nine-crest three-link alternating with nine-crest two-link patterns.

In the embodiments shown in FIGS. 11A-11B, 12A-12B and 13A-13B, all of the rings are positioned in an in-phase relationship, and all of the rings are connected by two links 32. The tubular body 20 has a compressed diameter and an expanded implanted diameter. Each embodiment differs in the number of crests or peaks in the rings. In the embodiment shown in FIGS. 11A-11B, stent 10 has a distal end 190, a proximal end 192, a distal end ring 194 and a proximal end ring 196. There are three body rings in between the distal end ring 194 and the proximal end ring 196. All of the rings have six crests or peaks 42, and all are in an in-phase relationship. The first body ring 198 is attached to the distal end ring 194 by two links 32, so that there are three peaks 42 in between each pair of links 32. The first body ring 198 is connected to the second body ring 200 by two links 32, and the second body ring 200 is connected to the third body ring 202 by two links 32. Since all of the rings have six peaks or crests 42, there will always be three peaks 42 in between each pair of links 32. The spacing between the links represents a cell 204 which is a big enough space to allow passage of an angioplasty catheter or a stent system to access a side branch vessel as discussed above. Each of the links 32 is connected to a valley 206 on one cylindrical ring and attached to a peak 208 on an adjacent cylindrical ring. If required, more rings can be added to the stent structure, however the six-crest and two-link in-phase stent design is maintained. Importantly, this embodiment has a high degree of flexibility and yet maintains an acceptable minimum amount of longitudinal strength against a compressive (or expansive) load. Although shown with a flexible non-linear link 32, a more longitudinally strong configuration with only a relatively straight section in the links may provide adequate flexibility in a design with only two links.

Figure 12A:
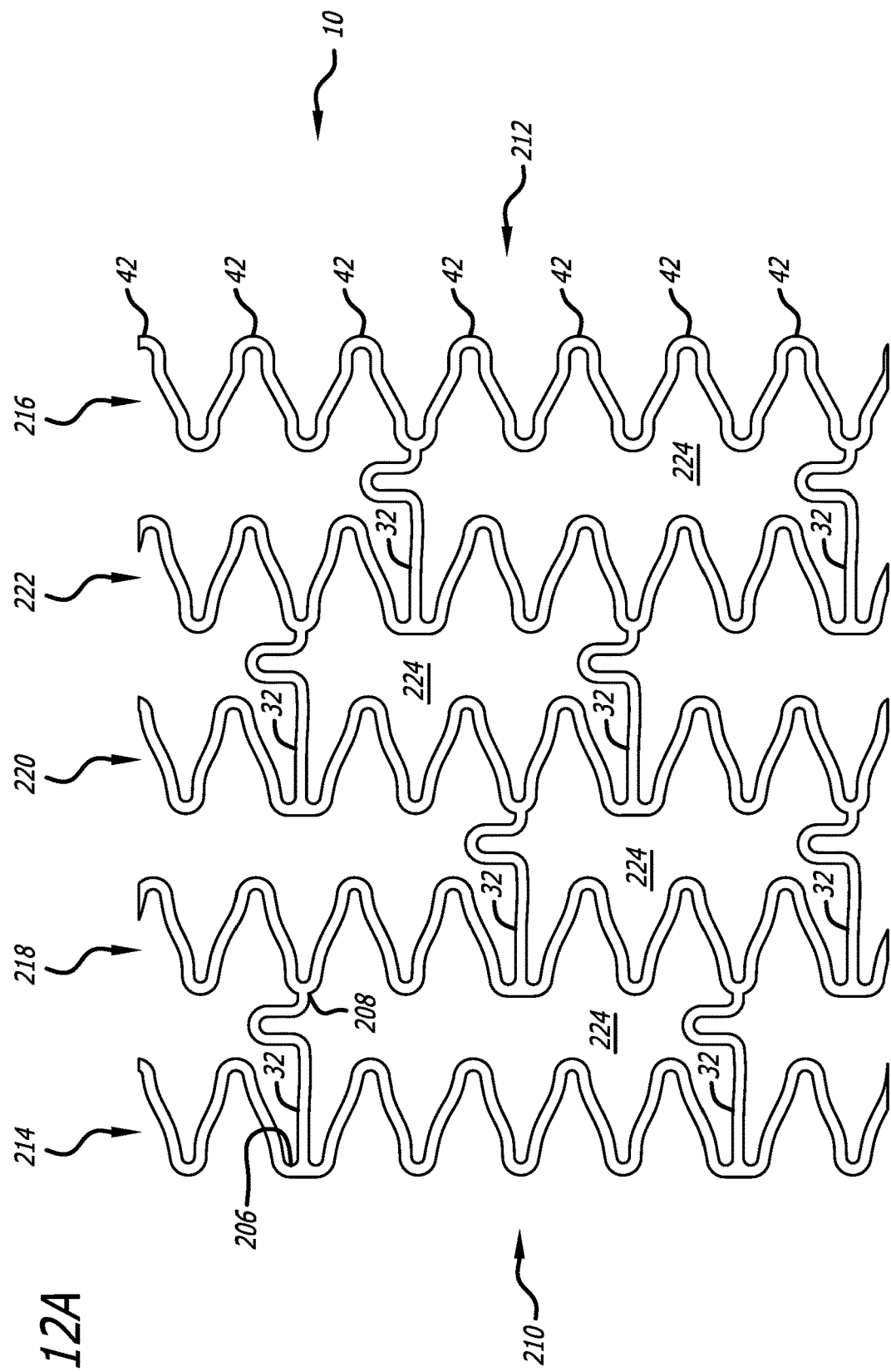
FIG. 12A is a plan view depicting one embodiment of the stent in a flattened configuration and illustrating the connecting link pattern between the end rings and the body rings.
Figure 12B:
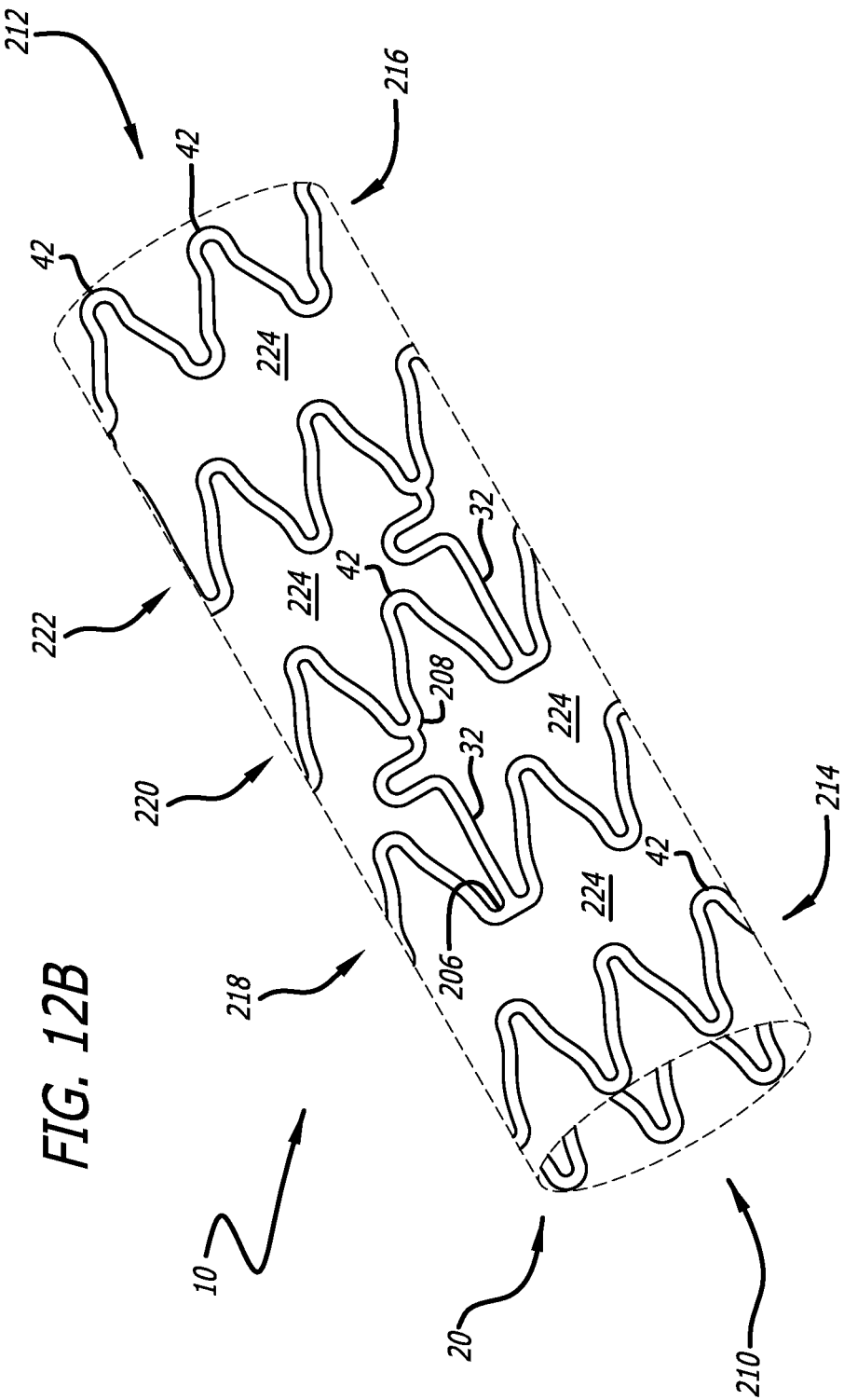
FIG. 12B is a perspective view of the stent of FIG. 12A in a tubular configuration.

In the embodiment shown in FIGS. 12A-12B, stent 10 has a distal end 210, a proximal end 212, a distal end ring 214, and a proximal end ring 216. The tubular body 20 has a compressed diameter and an expanded implanted diameter. There are three body rings in between the distal end ring 214 and the proximal end ring 216. All of the rings have seven crests or peaks 42, and all are in an in-phase relationship. The first body ring 218 is attached to the distal end ring 214 by two links 32, so that there are three peaks 42 in between each pair of links 32 in one circumferential direction and four peaks 42 in the other circumferential direction. The first body ring 218 is connected to the second body ring 220 by two links 32, and the second body ring 220 is connected to a third body ring 222 by two links 32. The spacing between the links represents a cell 224 which is a big enough space to allow passage of an angioplasty catheter or a stent system for treating the side branch vessel for an angioplasty, stenting, or some other procedure. Each of the links 32 is connected to a valley 206 on one cylindrical ring and attached to a peak 208 on an adjacent cylindrical ring. If required, more rings can be added to the stent structure, however the seven-crest and two-link in-phase stent design is maintained. Importantly, this embodiment has a high degree of flexibility and yet maintains an acceptable amount of longitudinal strength stability.

Figure 13A:
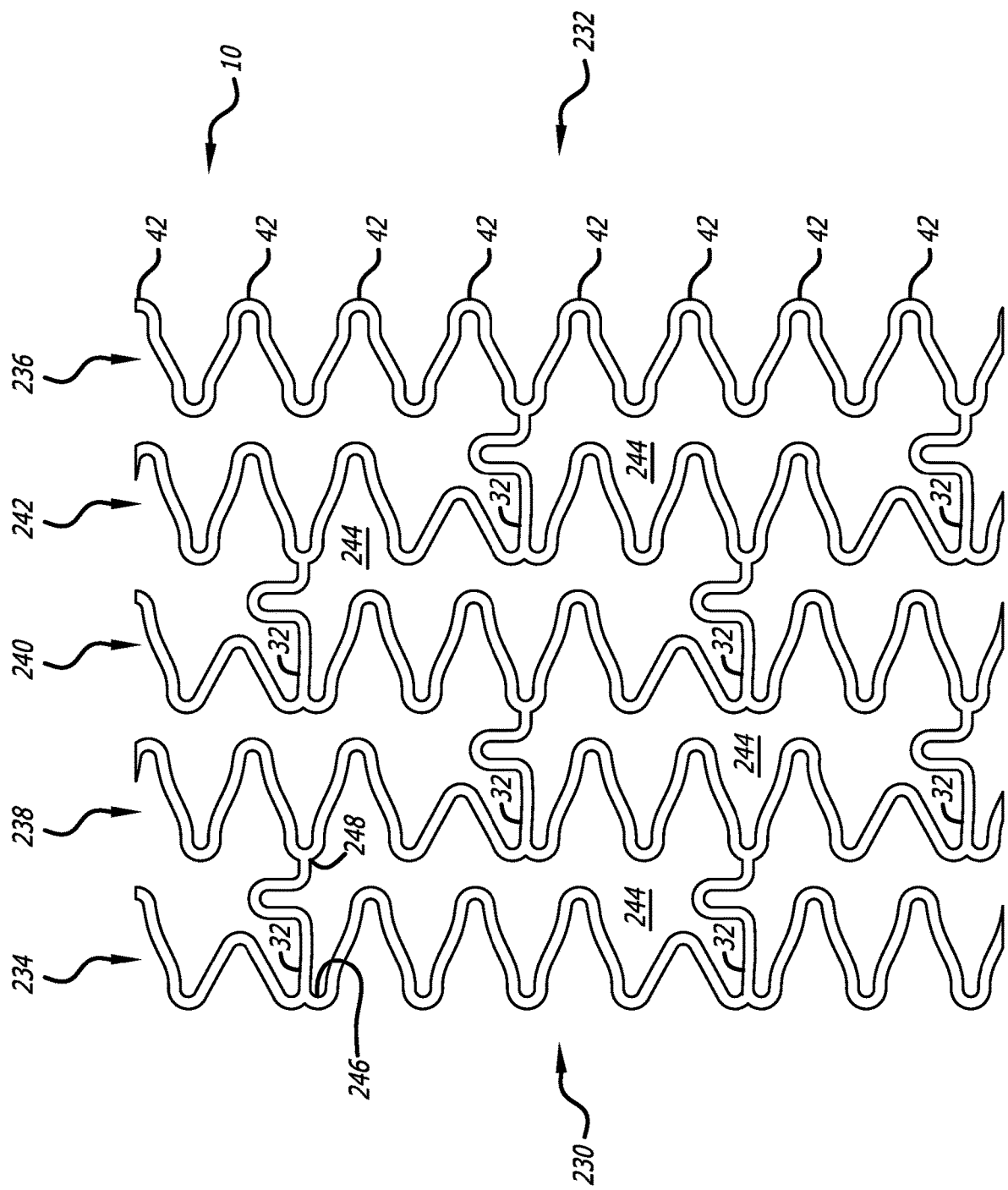
FIG. 13A is a plan view depicting one embodiment of the stent in a flattened configuration and illustrating the connecting link pattern between the end rings and the body rings.
Figure 13B:
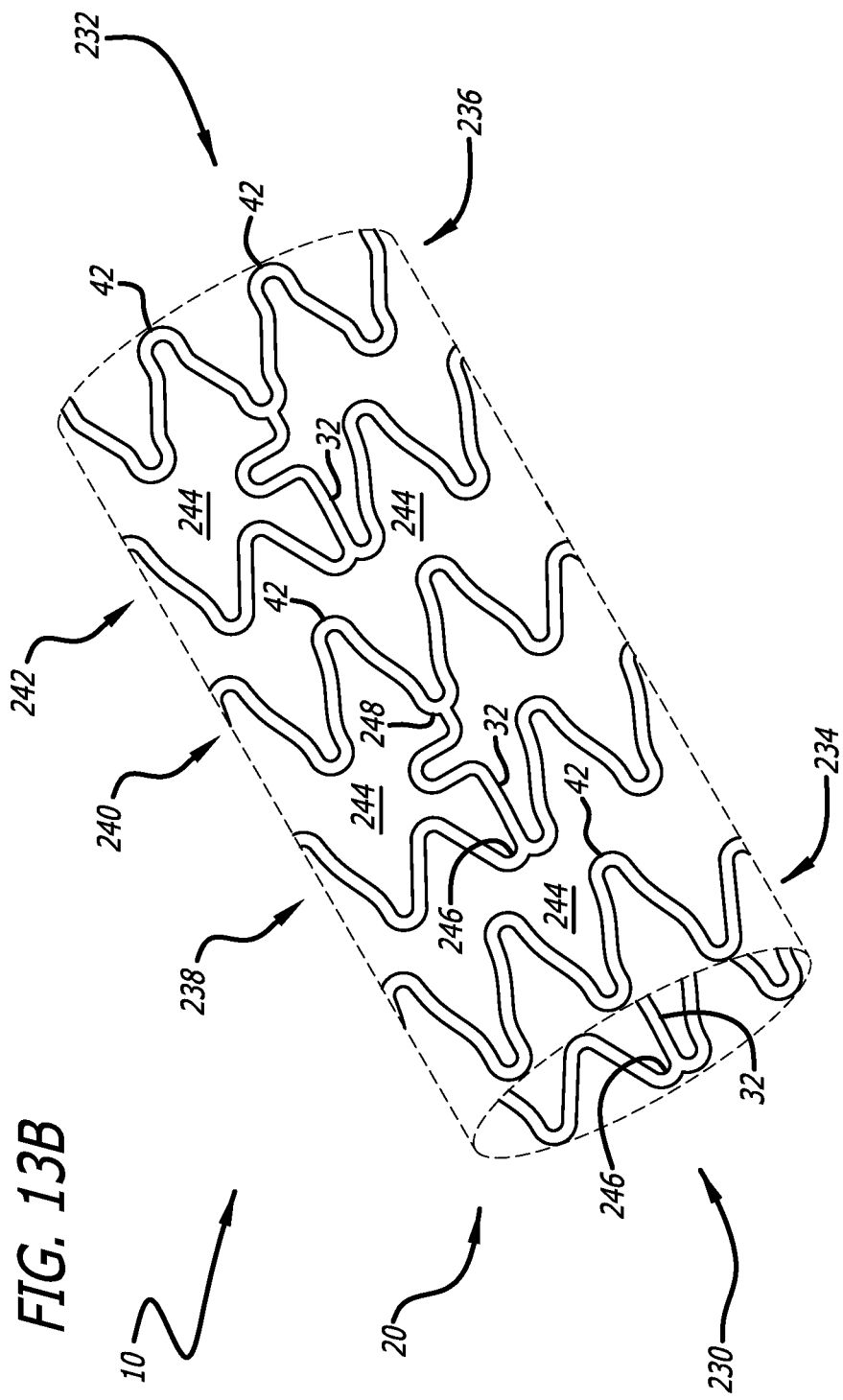
FIG. 13B is a perspective view of the stent of FIG. 13A in a tubular configuration.

In the embodiment shown in FIGS. 13A-13B, stent 10 has a distal end 230, a proximal end 232, a distal end ring 234, and a proximal end ring 236. The tubular body 20 has a compressed diameter and an expanded implanted diameter. There are three body rings in between the distal end ring 234 and the proximal end ring 236. All of the rings have eight crests or peaks 42, and all are in an in-phase configuration. The first body ring 238 is attached to the distal end ring 234 by two links 32, so that there are four peaks 42 in between each pair of links 32 in order to maintain design symmetry. The first body ring 238 is connected to the second body ring 240 by two links 32, and the second body ring 240 is connected to the third body ring 242 by two links 32. Since all of the rings have eight peaks or crests 42, there will always be four peaks 42 in between each pair of links 32. The spacing between the links represents a cell 244 which is a big enough space to allow passage of an angioplasty catheter or a stent for treating the side branch vessel for an angioplasty, stenting, or some other procedure. Each of the links 32 is connected to a valley 246 on one cylindrical ring and attached to a peak 248 on an adjacent cylindrical ring. If required, more rings can be added to the stent structure, however the eight-crest and two-link in-phase stent design is maintained. Importantly, this embodiment has a high degree of flexibility and yet maintains an acceptable amount of longitudinal strength stability.

Figure 14A:
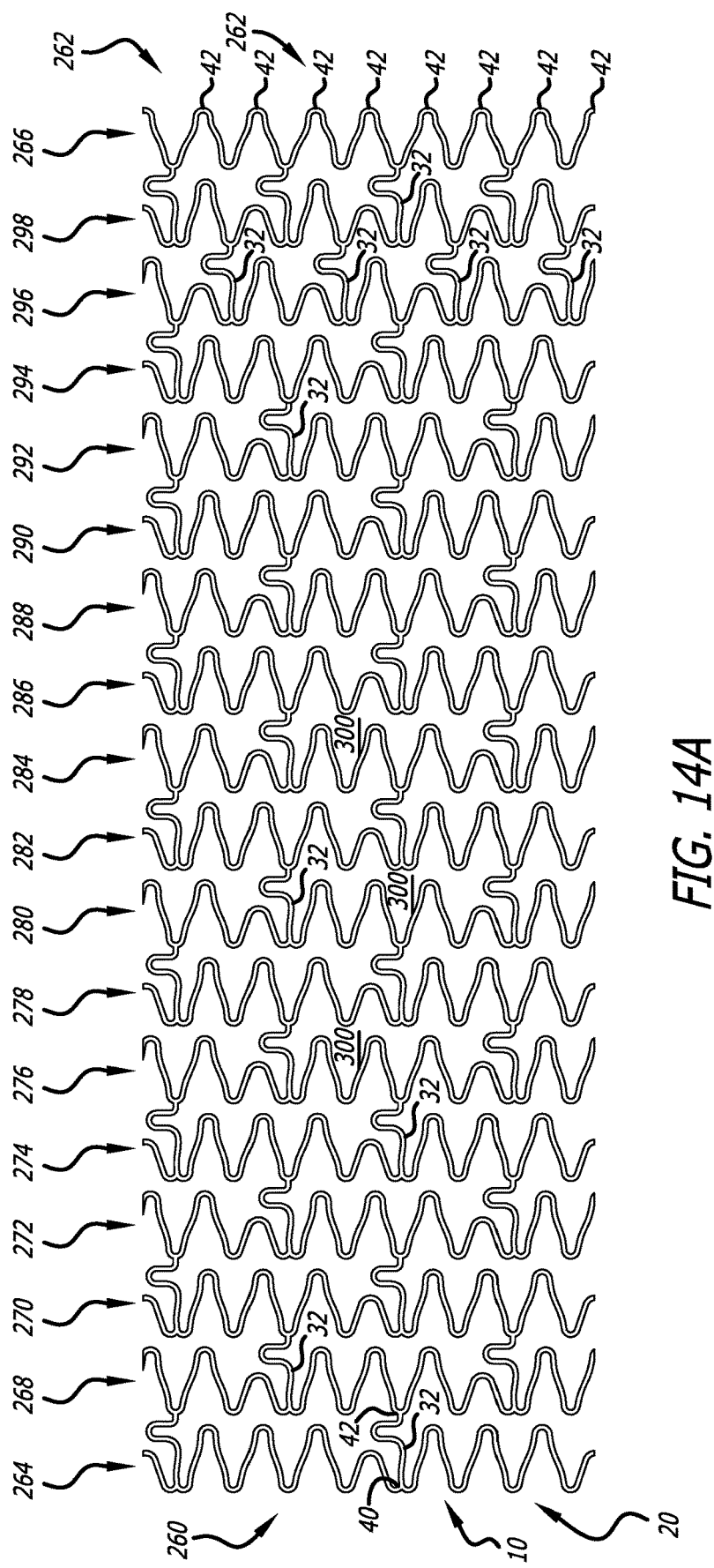
FIG. 14A is a plan view depicting one embodiment of the stent in a flattened configuration and illustrating the connecting link pattern between the end rings and the body rings.
Figure 14B:
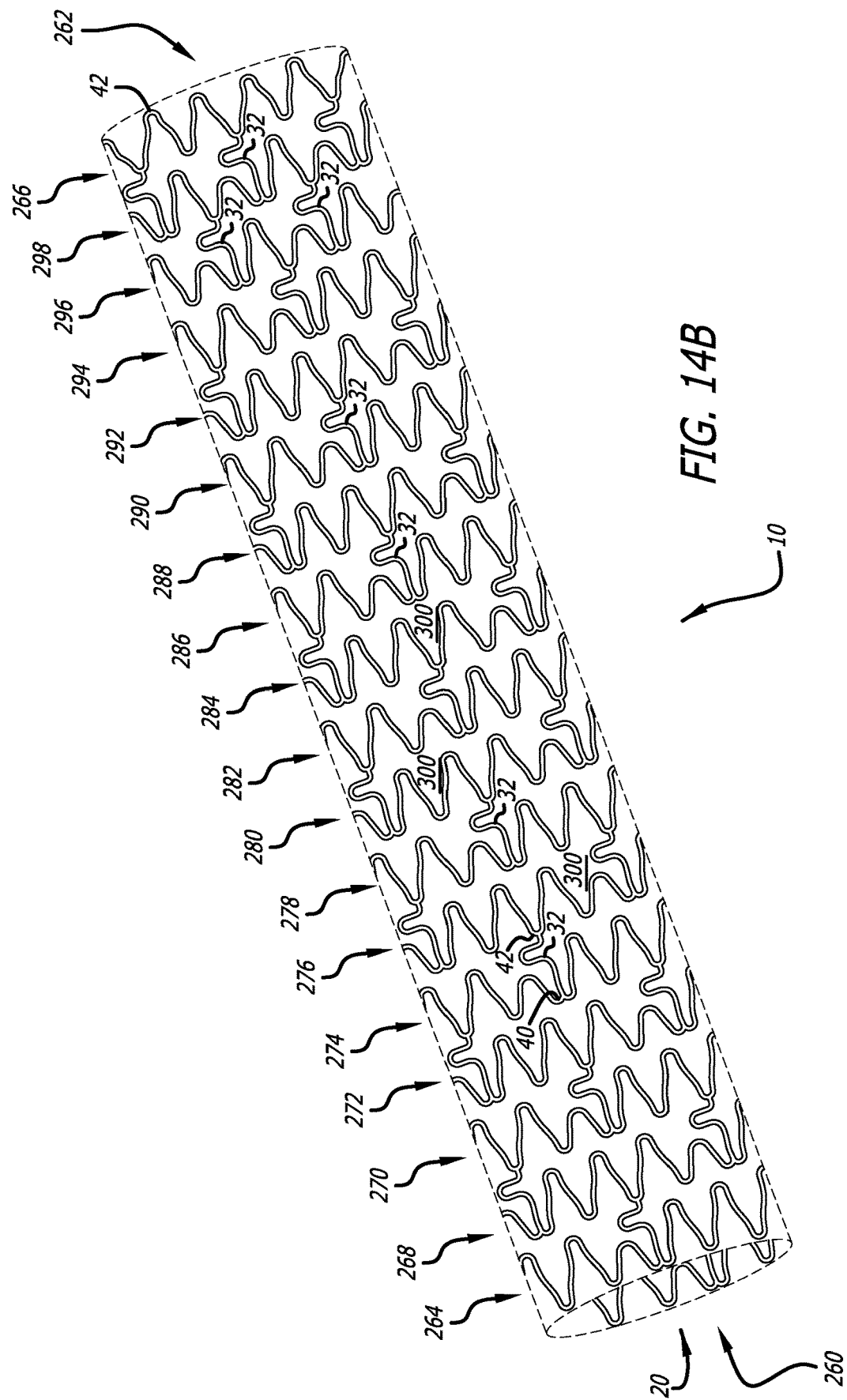
FIG. 14B is a perspective view of the stent of FIG. 14A in a tubular configuration.

In the FIGS. 14A and 14B embodiment, the stent 10 has eighteen eight-crest (or peaks 42) rings that are positioned in an in-phase relationship and are connected by links 32. The tubular body 20 has a compressed diameter and an expanded implanted diameter. The link configuration provides several portals for enhanced side branch vessel access and maximum flexibility on the distal end and maximum stability on the proximal end. The tubular body 20 has a distal end 260 and a proximal end 262. Basically, in this embodiment, the distal end ring 264 and the body rings 268-296 are all connected by two links 32. The two most proximal body rings 296 and 298 and the proximal end ring 266 are all connected by four links 32. The links 32 extend from a valley 40 of one ring to a peak 42 of the adjacent ring. The first body ring 268 is connected to a second body ring 270 by two links 32, the second body ring 270 is connected to a third body ring 272 by two links 32, the third body ring 272 is connected to a fourth body ring 274 by two links 32, the fourth body ring 274 is connected to a fifth body ring 276 by two links 32, the fifth body ring 276 is connected to a sixth body ring 278 by two links 32, the sixth body ring 278 is connected to a seventh body ring 280 by two links 32, the seventh body ring 280 is connected to an eighth body ring 282 by two links 32, the eighth body ring 282 is connected to a ninth body ring 284 by two links 32, the ninth body ring 284 is connected to a tenth body ring 286 by two links 32, the tenth body ring 286 is connected to an eleventh body ring 288 by two links 32, the eleventh body ring 288 is connected to a twelfth body ring 290 by two links 32, the twelfth body ring 290 is connected to a thirteenth body ring 292 by two links 32, the thirteenth body ring 292 is connected to a fourteenth body ring 294 by two links 32, the fourteenth body ring 294 is connected to a fifteenth body ring 296 by two links 32, the fifteenth body ring 296 is connected to a sixteenth body ring 298 by four links 32, and the sixteenth body ring 298 is connected to the proximal end ring 266 by four links 32. All of the rings have eight peaks or crests 42. The rings with four connecting links 32 provide structure to the design to minimize any compression under longitudinal forces, while the rings with two connecting links 32 reduce the chance of the side branch vessel being blocked by a link by one-third. The two-link rings can be referred to as portal rings. With portal rings, there is less of a need for precise positioning when implanting a stent in the main vessel and across a side branch vessel opening. If required, more rings connected by four links 32 can be added to the proximal end of the stent.

In FIGS. 14A, 14B, cells or portals 300 with only two links 32 connecting adjacent body rings increase the maximum size of the possible opening for side branch vessel access. There are four peaks or crests 42 in between each pair of links 32 providing maximum cell size. The maximum size of the opening (cells 300) is related to the path length of the cell 300 divided by pi and provides the maximum circular side branch access diameter (MCSBAD). The cells or portals 300 are big enough, when expanded, to permit access by a catheter or stent system for treating the side branch vessel for an angioplasty, stenting, or some other procedure.

One important feature of all of the embodiments of the present invention is the capability of the stents to expand from a low-profile diameter to a diameter much greater than heretofore was available, while still maintaining structural integrity in the expanded state and remaining highly flexible. Due to the novel structures, the stents of the present invention can have an overall expansion ratio of about 1.0 up to about 5.0 times the original diameter, or more, using certain compositions of stainless steel or cobalt chrome. For example, a 316L stainless steel stent or L605 cobalt chrome stent of the invention can be radially expanded from a diameter of 1.2 mm up to a diameter of about 5.75 mm, which deforms the structural members beyond the elastic limit. The stents still retain structural integrity in the expanded state and will serve to hold open the vessel in which they are implanted. Materials other than stainless steel (316L) may afford higher or lower expansion ratios without sacrificing structural integrity.

The stents of the present invention can be made in many ways. The preferred method of making the stent is to cut a thin-walled tubular member, such as a stainless steel or cobalt chrome tubing, to remove portions of the tubing in the desired pattern for the stent, leaving relatively untouched the portions of the metallic tubing which are to form the stent. It is preferred to cut the tubing in the desired pattern by means of a machine-controlled laser which is well known in the art. Electropolishing the stent is also well known in the art.

The stent tubing may be made of a suitable biocompatible material such as stainless steel, titanium, cobalt-chromium, tantalum, super-elastic (nickel-titanium) NiTi alloys and even high strength thermoplastic polymers. When stainless steel is utilized, the stainless steel can be one-eighth hardened due to a straightening process and then annealed to make the stent plastically deformable to thus remove intrinsic recoil post deployment. The stent diameters are very small, so the tubing from which it is made must necessarily also have a small diameter. For stents implanted in other body lumens, such as PTA applications in larger vessels like the renal artery, the dimensions of the tubing are correspondingly larger. The diameters and tubing wall thickness of the stents can vary according to a particular application and are known in the art. While it is preferred that the stents be made from laser cut tubing, those skilled in the art will realize that the stent can be laser cut from a flat sheet and then rolled up in a cylindrical configuration with the longitudinal edges welded or similarly joined to form a cylindrical shape.

It is preferred that the disclosed stent 10 have a constant strut thickness. In one embodiment, the radial thickness of all of the rings and links is approximately 68 micron. In another embodiment the thickness might be as large as 120 micron. While this dimension can vary depending upon the particular application, the 73 micron radial thickness provides optimum balance of flexibility to the stent, conformability to the vessel upon expansion, adequate radiopacity for viewing using fluoroscopy or other means of viewing, and adequate hoop strength in holding the artery open after the stent has been expanded and delivery balloon deflated. In some embodiments, there are six peaks 42 in each of the six rings and the overall stent length is between 8 and 48 mm.

The stents may also be made of materials such as super-elastic (sometimes called pseudo-elastic) nickel-titanium (NiTi) alloys. In this case, the stent would be formed full size but deformed diametrically (e.g. compressed) to a smaller diameter onto the delivery catheter to facilitate intraluminal delivery to a desired intraluminal site. The stress induced by the deformation transforms the stent from an austenite phase to a martensite phase to enable the compression into a capture sheath of the delivery catheter, and upon release of the compressive pressure when the stent reaches the desired intraluminal location, allows the stent to fully expand into the vessel due to the transformation of the nitinol back to the more stable austenite phase.

The present invention stent is ideally suited for drug delivery (i.e., delivery of a therapeutic agent) since it has a relatively uniform ratio of stent versus open surface area which ensures uniform distribution of drugs delivered within the vessel. Typically, a polymer is coated onto the stent of the type disclosed in U.S. Pat. Nos. 6,824,559 and 6,783,793 which are incorporated herein by reference.

These bioactive agents can be any agent, which is a therapeutic, prophylactic, or diagnostic. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include methyl rapamycin, ABT-578 (Zotarolimus), 40-O-(3-hydroxy)propyl-rapamycin, 40-O-[2-(2-hydroxy)ethoxy] ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprus side, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The bioactive agents also include metabolites of the foregoing substances and prodrugs of these metabolites. The foregoing substances are listed by way of example and are not meant to be limiting. Other active agents which are currently available or that may be developed in the future are equally applicable.

While the invention has been illustrated and described herein in terms of its use as intravascular stents, it will be apparent to those skilled in the art that the stents can be used in other instances in all vessels in the body. Since the stents of the present invention have the novel feature of expanding to very large diameters while retaining their structural integrity, they are particularly well suited for implantation in almost any vessel where such devices are or may be used. This feature, coupled with limited longitudinal contraction (i.e., stent length change or foreshortening) of the stent when it is radially expanded, provides a highly desirable support member for all vessels in the body. Other modifications and improvements may be made without departing from the scope of the invention.

We claim:

1. A stent, comprising:
   a tubular body having a length defined by a distal end ring and a proximal end ring and having a plurality of body rings including a first body ring, a second body ring, a third body ring, up to an Nth body ring therebetween;
   the end rings and the body rings being positioned in an in-phase relationship;
   the end rings and the body rings being connected by links having a pattern of 3 links-2 links-3 links along the length of the tubular body;
   wherein the links in the 2-link pattern are linear;
   the 3-link pattern further comprises non-linear links having a U-shaped non-linear portion and a curved elongated portion; and
   the distal end ring being connected to the first body ring by only three links, the first body ring being connected to the second body ring by only two links, the second body ring being connected to the third body ring by only three links, each of the remaining Nth body rings being connected by the pattern consisting of 3-2-3-2-3 links, and the proximal end ring being connected to the adjacent Nth body ring by only three links.

2. The stent of claim 1, wherein the non-linear links have both a linear portion and a non-linear portion.

3. The stent of claim 2, wherein each of the rings has a first crest and a second crest, the first crest being shorter than the second crest.

4. The stent of claim 3, wherein the stent has a compressed configuration and an expanded configuration, the non-linear portion of the non-linear link nests within the first crest when the stent is in the compressed configuration.

5. The stent of claim 1, wherein the stent is formed from a metal alloy taken from the group of metal alloys consisting of stainless steel, nickel-titanium, titanium, tantalum, and cobalt-chromium.

* * * * *